US012661035B2

(12) United States Patent (10) Patent No.: US 12,661,035 B2
Yamakawa et al. (45) Date of Patent: Jun. 23, 2026

(54) SUBSTANCE-IN-BLOOD CONCENTRATION MEASUREMENT DEVICE AND SUBSTANCE-IN-BLOOD CONCENTRATION MEASUREMENT METHOD

(71) Applicant: LIGHT TOUCH TECHNOLOGY INCORPORATED, Osaka (JP)

(72) Inventors: Koichi Yamakawa, Osaka (JP); Kanade Ogawa, Osaka (JP)

(73) Assignee: LIGHT TOUCH TECHNOLOGY INCORPORATED, Osaka (JP)

( * ) Notice: Subject to any disclaimer, the term of this patent is extended or adjusted under 35 U.S.C. 154(b) by 564 days.

(21) Appl. No.: 18/027,165

(22) PCT Filed: Sep. 29, 2021

(86) PCT No.: PCT/JP2021/035990
§ 371 (c)(1),
(2) Date: Mar. 20, 2023

(87) PCT Pub. No.: WO2022/071442
PCT Pub. Date: Apr. 7, 2022

(65) Prior Publication Data
US 2023/0355142 A1 Nov. 9, 2023

(30) Foreign Application Priority Data
Sep. 30, 2020 (JP) ................................ 2020-165688

(51) Int. Cl.
*A61B 5/1455* (2006.01)
*G01N 21/49* (2006.01)

(52) U.S. Cl.
CPC ........... *A61B 5/1455* (2013.01); *G01N 21/49* (2013.01)

(58) Field of Classification Search
CPC . A61B 5/1455; A61B 5/14552; A61B 5/0059; A61B 5/6826; A61B 2562/0233; A61B 2562/0242
See application file for complete search history.

(56) References Cited

U.S. PATENT DOCUMENTS 5,598,842 A * 2/1997 Ishihara ............... A61B 5/0261
600/322
7,697,966 B2 * 4/2010 Monfre ................ A61B 5/1455
600/310
(Continued)

FOREIGN PATENT DOCUMENTS

JP 2001-153796 A 6/2001
JP 2009-168670 A 7/2009
(Continued)

OTHER PUBLICATIONS

International Search Report and Written Opinion mailed on Dec. 14, 2021, received for PCT Application PCT/JP2021/035990, filed on Sep. 29, 2021, 17 pages including English Translation.
Ruochong Zhang et al., "Noninvasive Electromagnetic Wave Sensing of Glucose", Sensors, vol. 19., No. 5, Mar. 7, 2019 p. 1151, XP055944049, DOI: 10.3390/s19051151, 20pp.
Extended European Search Report issued Feb. 13, 2024, in corresponding European Patent Application No. 21875739.1, 9pp.

*Primary Examiner* — Eric F Winakur
(74) *Attorney, Agent, or Firm* — XSENSUS LLP

(57) ABSTRACT
A substance-in-blood concentration measurement device for measuring concentration of a substance in blood of a living body, including: a target placement unit on which the living body that includes a measurement target portion is placed; a light emission unit that irradiates the measurement target portion with a laser beam; a photodetector that receives reflected light from the measurement target portion and detects intensity of the reflected light; and a condenser lens disposed on an optical path of the reflected light between the measurement target portion and the photodetector. On the optical path from the measurement target portion to the photodetector, in a section from the target placement unit to
(Continued)

the photodetector, the reflected light propagates through space, except where transmitted through the condenser lens, and the condenser lens forms an image of the reflected light on the photodetector.

24 Claims, 17 Drawing Sheets

(56)                    References Cited

U.S. PATENT DOCUMENTS 9,301,694 B2 *    4/2016  Gu ..................... A61B 5/14551
2018/0335381 A1    11/2018  Bauer et al.

FOREIGN PATENT DOCUMENTS

| JP | 2010-276407 A | 12/2010 |
| JP | 2017-509373 A | 4/2017 |
| JP | 2018-141761 A | 9/2018 |
| JP | 2018-157928 A | 10/2018 |
| JP | 2018-534031 A | 11/2018 |
| JP | 2019-507320 A | 3/2019 |
| WO | 2016/117520 A1 | 7/2016 |

* cited by examiner

FIG. 3

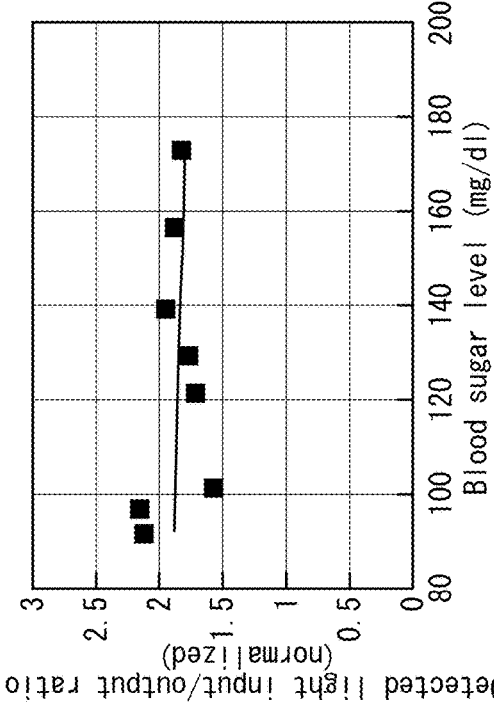
FIG. 6B
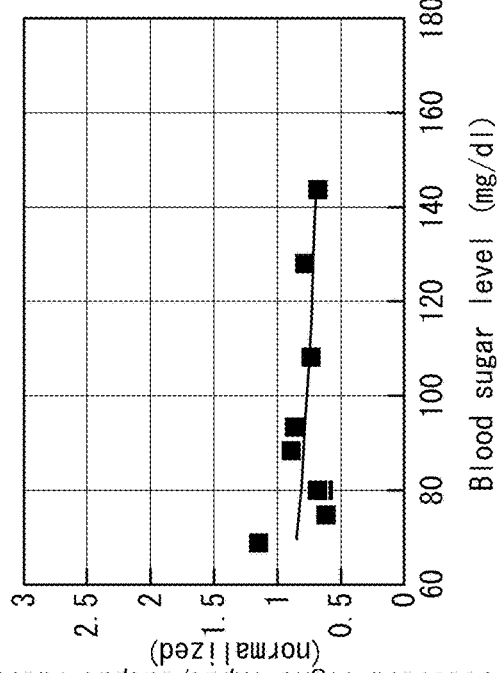
FIG. 6D
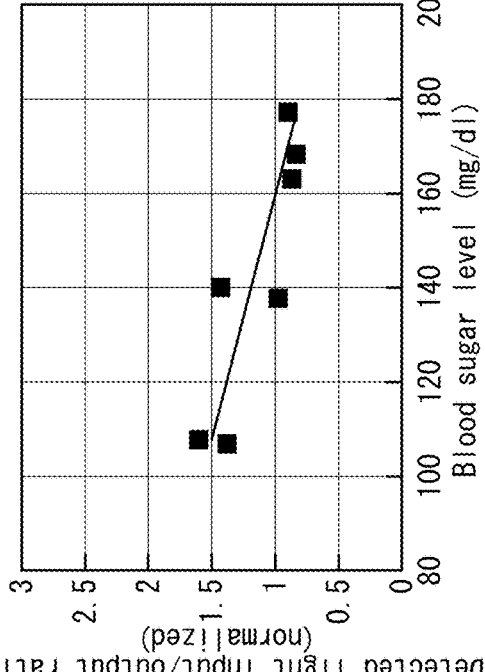
FIG. 6A
FIG. 6C $\theta$ : 65 degrees

F : 25.4

L : 2F, 2F−0.5, 2F+0.5

$\Phi$ : 25, 35, 40 degrees

SUBSTANCE-IN-BLOOD CONCENTRATION MEASUREMENT DEVICE AND SUBSTANCE-IN-BLOOD CONCENTRATION MEASUREMENT METHOD

CROSS-REFERENCE TO RELATED APPLICATIONS

The present application is based on PCT filing PCT/JP2021/035990, filed Sep. 29, 2021, which claims priority to JP 2020-165688, filed Sep. 30, 2020, the entire contents of each are incorporated herein by reference.

TECHNICAL FIELD

The present disclosure relates to devices and methods that measure concentrations of substances in blood flowing through blood vessels of living organisms by noninvasive measurement methods.

BACKGROUND ART

In prevention and treatment of lifestyle-related diseases, it is important to routinely check substance-in-blood levels such as blood sugar levels and blood lipid levels. In particular, patients with diabetes, which is one such lifestyle-related disease, are required to routinely measure concentration of glucose in their blood and manage blood sugar levels in order to prevent complications, and conventionally, an invasive method of sampling blood and performing a chemical analysis is used.

Regarding this, in recent years, simple noninvasive methods for optically measuring the state of blood in a living body without blood sampling have been proposed. For example, Patent Literature 1 discloses a substance-in-blood concentration measurement device that measures blood glucose concentration using a simple noninvasive structure by which a living body is irradiated with high-intensity mid-infrared light via a waveguide and reflected light is guided through the waveguide to a photodetector.

CITATION LIST

Patent Literature

[Patent Literature 1] WO 2016/117520

SUMMARY OF INVENTION

Technical Problem

However, according to the conventional substance-in-blood concentration measurement device using a waveguide described in Patent Literature 1, there is a problem that measured values vary and it is difficult to perform stable and standardized measurement due to changes in condition of a skin surface of the living body to be measured and slight changes in condition of emitted laser light.

The present disclosure is made in view of the above problem, and an object of the present disclosure is to provide a substance-in-blood concentration measurement device and a substance-in-blood concentration measurement method capable of stably performing high-accuracy measurement regardless of changes in state of the measurement target and laser beam emission conditions.

Solution to Problem

In order to achieve the above object, the substance-in-blood concentration measurement device pertaining to an aspect of the present disclosure is for measuring concentration of a substance in blood of a living body and includes: a target placement unit on which the living body that includes a measurement target portion is placed; a light emission unit that irradiates the measurement target portion with a laser beam; a photodetector that receives a reflected light component of the laser beam reflected from the measurement target portion and detects intensity of the reflected light; and a first lens disposed on an optical path of the reflected light between the measurement target portion and the photodetector. On the optical path from the measurement target portion to the photodetector, in a section from the target placement unit to the photodetector, the reflected light propagates through space, except where transmitted through the first lens, and the first lens forms an image of the reflected light on the photodetector.

Advantageous Effects of Invention

According to the substance-in-blood concentration measurement device and the substance-in-blood concentration measurement method pertaining to an aspect of the present disclosure, highly accurate measurement is stably performed regardless of changes in state of the measurement target and laser beam emission conditions.

BRIEF DESCRIPTION OF DRAWINGS

FIG. 3 is a schematic diagram illustrating structure of a light emission unit 20 in the substance-in-blood concentration measurement device 1.

FIG. 6A, 6B, 6C, 6D are diagrams illustrating correlation between glucose concentration measurements by the photodetector and glucose concentration measurements by the invasive measurement device of FIG. 5A, 5B, 5C, 5D.

FIG. 14 is a schematic diagram illustrating structure of a substance-in-blood concentration measurement device 1A according to Embodiment 2.

FIG. 15 is a schematic diagram illustrating an operation adjusting optical path length from measurement target portion Mp to the photodetector 30, according to the substance-in-blood concentration measurement device 1A.

DESCRIPTION OF EMBODIMENTS

Circumstances Leading to Embodiments

Figure 17:
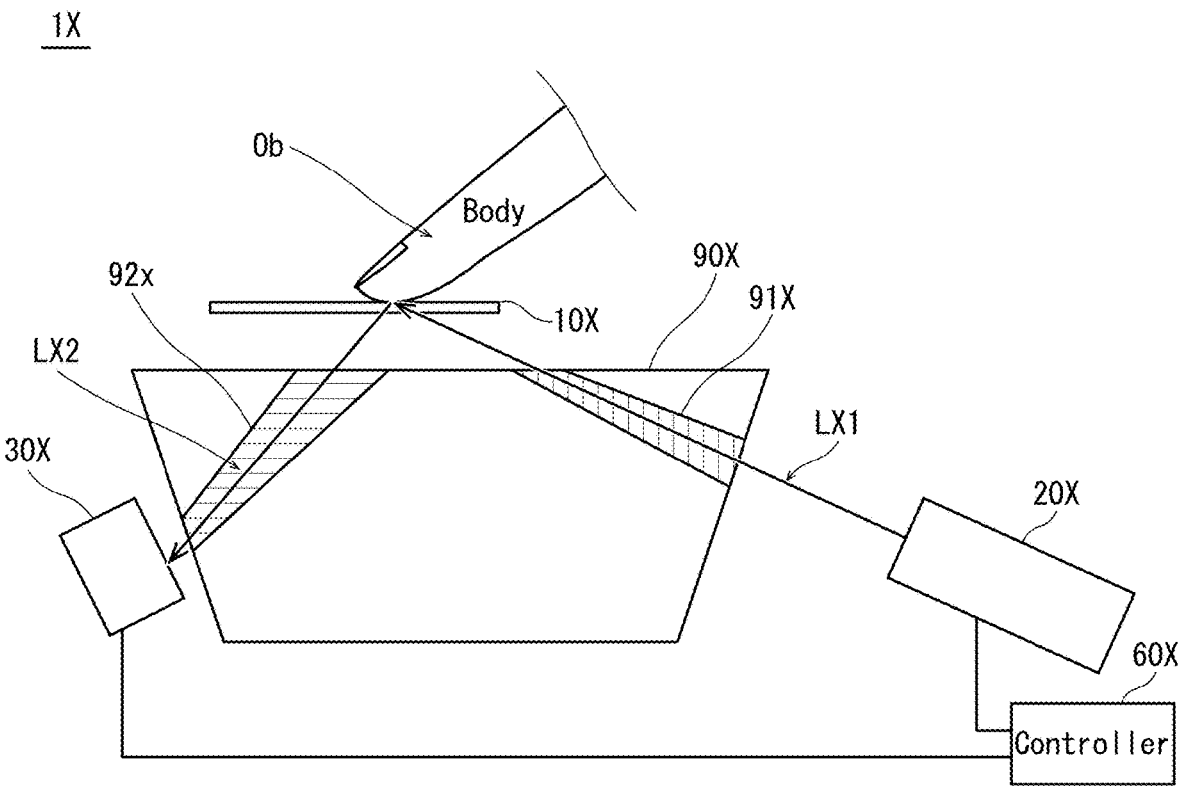
FIG. 17 is a schematic diagram illustrating structure of the conventional substance-in-blood concentration measurement device 1X.

In recent years, noninvasive substance-in-blood concentration measurement methods that do involve blood sampling have been proposed for routine blood sugar level management and the like for diabetic patients. FIG. 17 is a schematic diagram illustrating structure of a conventional substance-in-blood concentration measurement device 1X (hereinafter also referred to as "device 1X") using a noninvasive method, as disclosed in Patent Literature 1.

As illustrated in FIG. 17, the device 1X includes a target placement unit 10X on which a living body Ob to be examined is placed, a light emission unit 20X that emits a pulsed laser beam L1 composed of mid-infrared light, a light guide unit 90X in which an incident side waveguide 91X and an exit side waveguide 92X are provided, both of which are holes through the light guide unit 90X, a photodetector 30X that receives light LX2 reflected from the living body Ob and detects intensity of the light LX2, and a controller 60X. Patent Literature 1 describes that the device 1X is able to measure blood glucose concentration noninvasively with a simple structure by irradiation of high intensity mid-infrared light However, as mentioned above, experiments by the inventors revealed that, according to the device 1X using the noninvasive method, measured values vary due to factors such as the state of the skin surface of the living body being measured and slight changes in emitted laser light conditions, making it difficult to perform stable standardized measurements.

According to investigation by the inventors, two light components being detected together without separation by the photodetector, a light component reflected from the skin surface and a light component reflected from a portion of the living body below the skin surface that contains blood sugar, which is the intended measurement target, is considered to be a factor in variation of measured values. In order to solve this problem, it is necessary, for example, to set an optical system for each subject and measurement so as to be suitable for the subject's biological conditions and measurement conditions. However, a high degree of skill is required to adjust an optical system appropriately for each subject and measurement, and a patient being responsible for their own routine measurements of blood glucose levels greatly impairs the convenience of such a noninvasive method.

Here, as a result of intensive studies into optical system configurations in noninvasive substance-in-blood concentration measurement methods that achieve stable high-accuracy measurement regardless of changes in state of a measurement target and changes in laser beam irradiation conditions, the inventors have achieved the following embodiments.

Overview of Embodiments

The substance-in-blood concentration measurement device according to at least one embodiment of the present disclosure is for measuring concentration of a substance in blood of a living body and includes: a target placement unit on which the living body that includes a measurement target portion is placed; a light emission unit that irradiates the measurement target portion with a laser beam; a photodetector that receives a reflected light component of the laser beam reflected from the measurement target portion and detects intensity of the reflected light; and a first lens disposed on an optical path of the reflected light between the measurement target portion and the photodetector. On the optical path from the measurement target portion to the photodetector, in a section from the target placement unit to the photodetector, the reflected light propagates through space, except where transmitted through the first lens, and the first lens forms an image of the reflected light on the photodetector.

According to this structure, when compared to a conventional device that uses a waveguide, the substance-in-blood concentration measurement device reduces a false signal (noise) component of reflected light scattered from the skin surface, improving S/N ratio. Therefore, highly accurate light measurement is normally possible regardless of skin surface conditions, which vary from subject to subject and measurement to measurement. As a result, an easily configured substance-in-blood concentration measurement device capable of stably performing highly accurate measurement regardless of change in state of the measurement target and laser beam irradiation conditions is provided. As a result, it is possible to eliminate the work of adjusting the optical system for each living body or each measurement in routine blood sugar level measurement performed by a patient, thereby realizing a noninvasive and simple measurement method.

According to at least one embodiment, the light emission unit irradiates the measurement target portion with the laser beam from a back surface side opposite a body placement side of the target placement unit, and the photodetector receives the reflected light component of the laser beam reflected from the measurement target portion from the back surface side of the target placement unit.

According to this structure, an optical system of an optical measurement device is realized that reduces false signals (noise) components from reflected light scattered from the skin surface.

According to at least one embodiment, the measurement target portion is a portion of the living body inwards of the epidermis, and the first lens transfers an area irradiated by the laser beam in the measurement target portion to a light receiving surface of the photodetector.

According to this structure, a degree of influence of a light component reflected from the skin surface detected as noise is small, and a light component reflected from a body portion inwards of the skin surface that should be a primary measurement target portion is imaged on the screen of the photodetector to influence optical measurement by the photodetector. Accordingly, highly reproducible measurement can be performed.

According to at least one embodiment, the substance-in-blood concentration measurement device further includes a second lens disposed on the optical path of the laser beam between the light emission unit and the measurement target portion, the second lens condensing the laser beam on the measurement target portion. On the optical path from the light emission unit to the measurement target portion, in a section from the light emission unit to the target placement unit, the laser beam propagates through space, except where transmitted through the second lens.

According to this structure, the laser beam emitted from the light emission unit is focused to a depth corresponding to a portion of the living body inwards of the epidermis corresponding to the measurement target portion that is a defined distance from the surface of the target placement unit At this time, irradiation area of the laser beam can be reduced in size according to the measurement target portion.

According to at least one embodiment, the light receiving surface of the photodetector is separated from the first lens by a defined distance more than a distance from the first lens to a position to which an image of light reflected from a skin surface of the living body is transferred.

According to this structure, the area irradiated by light in the measurement target portion that corresponds to the portion of the living body inwards of the epidermis is transferred to the position of the photodetector.

According to at least one embodiment, depth from a skin surface of the living body to the measurement target portion is changed by changing a position of the photodetector.

According to this structure, by adjusting the position of the photodetector, it is possible to change the optical path length L on the light receiving side, making it possible to handle measurement targets having thick skin.

According to at least one embodiment, an incident angle of the laser beam to the measurement target portion is different from an emission angle of the optical path from the measurement target portion to the photodetector.

According to this structure, the influence of regular reflection of incident light is suppressed.

According to at least one embodiment, the emission angle of the optical path from the measurement target portion to the photodetector is from 0 degrees to 90 degrees from the normal to a surface of the target placement unit on which the living body is placed, and is different from the incident angle of the laser beam to the measurement target portion.

According to at least one embodiment, the incident angle of the laser beam to the measurement target portion is 45 degrees or more from the normal to a surface of the target placement unit on which the living body is placed, and emission angle of the optical path from the measurement target portion to the photodetector is from 0 degrees to 40 degrees from the normal to the surface.

According to this structure, an optical system is realized that takes stable measurements where glucose light absorption is relatively large and there is no increase in signals due to regular reflection in a range of buildable receiving-side optical systems and emission-side optical systems.

According to at least one embodiment, wavelength of the laser beam is a defined wavelength selected from a range from 2.5 μm to 12 μm.

According to this structure, absorption by glucose is greater than that of conventional near-infrared light, and blood glucose concentration can be measured. Compared to near-infrared light conventionally used to measure blood sugar levels, mid-infrared light has lower transmittance into the living body, and therefore only the skin region is measured, obtaining an effect of being less influenced by other biological components deeper than the epidermis.

According to at least one embodiment, modulating the wavelength of the laser beam allows for detection of different types of blood component.

According to this structure, a plurality of different blood components may be detected by selectively emitting the laser beam at different wavelengths with the same measurement device.

According to at least one embodiment, the wavelength of the laser beam is a defined wavelength selected from a range from 6.0 μm to 12 μm, and a blood component to be detected is glucose. Here, the wavelength may be selected in a range from −0.05 μm to +0.05 μm from a value of 7.05 μm, 7.42 μm, 8.31 μm, 8.7 μm, 9.0 μm, 9.26 μm, 9.57 μm, 9.77 μm, 10.04 μm, or 10.92 μm.

According to this structure, absorption by glucose is greater than that of near-infrared light, and transmittance is low, so measurement of only the skin region is possible, and blood glucose concentration can be stably measured.

According to at least one embodiment, the wavelength of the laser beam is a defined wavelength selected from a range from 5.0 μm to 12 μm, and a blood component to be detected is lactic acid. Here, the wavelength may be selected in a range from −0.05 μm to +0.05 μm from a value of 5.77 μm, 6.87 μm, 7.27 μm, 8.23 μm, 8.87 μm, or 9.55 μm.

According to this structure, lactic acid concentration in blood can be measured.

According to at least one embodiment, the photodetector comprises an infrared sensor that outputs an intensity of the reflected light as a one-dimensional value, and the substance-in-blood concentration measurement device further includes a two-dimensional imaging means that may be disposed in a position relative to the measurement target portion that is equivalent to the position relative to the measurement target portion of the photodetector, the two-dimensional imaging means receiving the reflected light reflected from the measurement target portion to detect whether or not a focused image is formed based on the reflected light.

According to this structure, a process of adjusting optical path length from the measurement target portion to the photodetector in order to focus light reflected from the measurement target portion onto the photodetector can be performed by replacing the photodetector with the two-dimensional imaging means.

According to at least one embodiment, the photodetector is a two-dimensional infrared sensor array in which a plurality of light receiving elements capable of detecting mid-infrared light are arranged in a matrix on a light receiving surface.

According to this structure, a process of adjusting optical path length from the measurement target portion to the photodetector in order to focus light reflected from the measurement target portion onto the photodetector can be performed by using the photodetector itself.

According to at least one embodiment, the target placement unit is provided with a through hole in an area where a surface of the living body comes into contact with the target placement unit, the laser beam irradiates the surface of the living body through the through hole, and the reflected light is received by the photodetector through the through hole.

According to this structure, total reflection at a surface of the living body Ob is suppressed, and the laser beam emitted from the light emission unit directly irradiates the surface of the living body, improving laser beam intensity.

According to at least one embodiment, the target placement unit is provided with a concave portion in an area where a surface of the living body comes into contact with the target placement unit, the laser beam irradiates the surface of the living body by passing through the target placement unit, and the reflected light is received by the photodetector by passing through the target placement unit.

According to this structure, total reflection at a surface of the living body is suppressed, and since the target placement unit does not have an opening, dust, dirt, water vapor, and the like is prevented from entering the environment where optical systems such the light emission unit are disposed, providing the target placement unit with a dustproofing function The substance-in-blood concentration measurement method according to an embodiment of the present disclosure is for measuring concentration of a substance in blood of a living body, and includes: a target placement step of placing the living body that includes a measurement target portion; a light emission step of irradiating the measurement target portion with a laser beam from a light emission unit; an imaging step of forming an image of light reflected from the measurement target portion onto a photodetector using a first lens disposed between the measurement target portion and the photodetector; and a photodetection step of receiving the reflected light with the photodetector and detecting intensity of the reflected light According to this method, high accuracy measurement may be stably performed regardless of changes in state of the measurement target and irradiation conditions of the laser beam.

According to at least one embodiment, in the light emission step, the laser beam is condensed onto the measurement target portion by using a second lens disposed between the light emission unit and the measurement target portion.

According to this method, the laser beam emitted from the light emission unit is focused to a depth corresponding to a portion of the living body inwards of the skin surface corresponding to the measurement target portion that is a defined distance from the surface of the target placement unit According to at least one embodiment, in the imaging step, on the optical path from the measurement target portion to the photodetector, in a section from a target placement unit to the photodetector, the reflected light propagates through space, except where transmitted through the first lens, and in the light emission step, on the optical path from the light emission unit to the measurement target portion, in a section from the light emission unit to the target placement unit, the laser beam propagates through space, except where transmitted through the second lens.

According to at least one embodiment, in the light emission step, the measurement target portion is irradiated by the laser beam from a back surface side opposite a body placement side of the target placement unit, and in the imaging step, the photodetector receives the reflected light component of the laser beam reflected from the measurement target portion from the back surface side of the target placement unit.

According to this method, a process of imaging light reflected from the measurement target portion onto the photodetector is specifically realized.

According to at least one embodiment, the substance-in-blood concentration measurement method further includes, prior to the imaging step, an adjustment step of adjusting an optical path length from the measurement target portion to the photodetector so that the light reflected from the measurement target portion forms a focused image on the photodetector.

According to this method, light reflected from the measurement target portion onto the photodetector is focused.

According to at least one embodiment, the adjustment step includes causing a two-dimensional imaging means disposed in a position relative to the measurement target portion that is equivalent to the position relative to the measurement target portion of the photodetector to receive the reflected light reflected from the measurement target portion, and detecting whether or not the focused image is formed based on the reflected light.

According to this method, a process of adjusting optical path length from the measurement target portion to the photodetector in order to focus light reflected from the measurement target portion onto the photodetector can be performed by replacing the photodetector with the two-dimensional imaging means.

Embodiment 1

A substance-in-blood concentration measurement device 1 according to the present embodiment is described with reference to the drawings. In this description, a positive direction in a height direction may be referred to as an "upwards" direction, and a negative direction as a "downwards" direction, while a surface facing the positive height direction may be referred to as a "front" surface and a surface facing the negative height direction may be referred to a "rear" surface. Further, elements in each drawing are not necessarily drawn to scale. Further, in this description, a numerical range indicated by the symbol "-" or "from . . . to . . . " includes values at both ends of the numerical range. Further, materials, numerical values, and the like described herein are only preferred examples, and are not limiting.

Overall Structure

The substance-in-blood concentration measurement device 1 (hereinafter also referred to as "device 1") is a medical device that irradiates a measurement target portion of a living body with a laser beam of a specific wavelength from a light source, and noninvasively measures concentration of a substance in the blood of a living body at the measurement target portion by detecting intensity of light reflected from the measurement target portion. The laser beam uses light of the specific wavelength that is absorbable by the substance to be measured. When the substance-in-blood concentration is high, the absorption by the substance reduces the intensity of the light reflected from the measurement target portion, and therefore the device 1 measures the substance-in-blood concentration by measuring the intensity of reflected light with a photodetector. According to the present embodiment, as an example, the substance-in-blood to be measured is glucose, and the laser beam used is light having a wavelength selected from mid-infrared light, and a predefined wavelength selected from a range from 2.5 μm to 12 μm may be used. More preferably, a predefined wavelength selected from a range from 6.0 μm to 12 μm may be used. More specifically, for example, 9.26±0.05 μm (9.21 μm to 9.31 μm) may be used. Alternatively, a range from −0.05 μm to +0.05 μm from a wavelength of 7.05 μm, 7.42 μm, 8.31 μm, 8.7 μm, 9.0 μm, 9.57 μm, 9.77 μm, 10.04 μm, or 10.92 μm may be used. Thus, glucose concentration in epithelial interstitial fluid is measurable as a blood sugar level. In this case, it is necessary to measure glucose concentration in interstitial fluid directly under skin, and mid-infrared light is preferably used, which is highly absorbed and therefore does not penetrate deeply into the living body. Further, use of mid-infrared light reduces influence of overtones and combination tones, meaning glucose may be measured more accurately than with near-infrared light.

Figure 1:
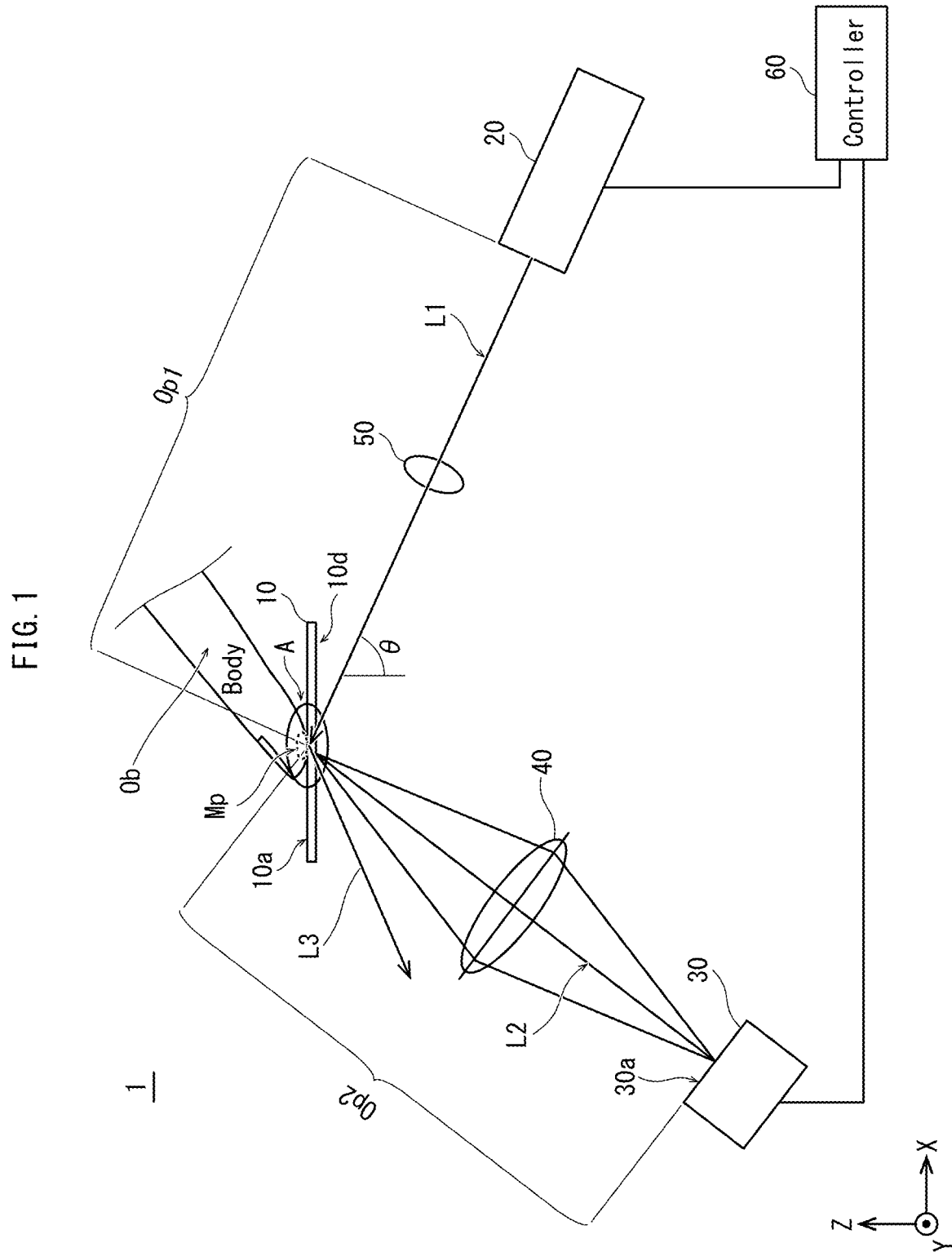
FIG. 1 is a schematic diagram illustrating structure of a substance-in-blood concentration measurement device 1 according to Embodiment 1.

FIG. 1 is a schematic diagram illustrating structure of the device 1 according to Embodiment 1. As illustrated in FIG. 1, the device 1 includes a target placement unit 10, a light emission unit 20, a photodetector 30, a condenser lens 50, an imaging lens 40, and a controller 60.

<Element Structure>

The following describes structures of elements of the device 1.

(Target Placement Unit 10)

The target placement unit 10 is a plate-like guide member for regulating, by contact between a front surface 10a and a skin surface of a living body Ob, a measurement target portion Mp of the living body Ob to a defined position and angle suitable for measurement In this case, the front surface 10a of the target placement unit 10 may also be referred to as a body placement surface. By covering the optical system such as the light emission unit 20 with a housing (not shown) and providing the target placement unit 10 to an outer shell of the housing, the target placement unit 10 is able to function as an irradiation window irradiated by the laser beam L1 from inside.

The target placement unit 10 is made of a material such as ZnSe that is transmissive to mid-infrared light at a specific wavelength used for measurement, and may be provided with an anti-reflection coating on the front surface. A measurement position is marked on the front surface 10a of the target placement unit 10. When the living body Ob including the measurement target portion Mp is aligned with the measurement position and the living body Ob is pressed onto the front surface 10a of the target placement unit 10 with a defined pressure, the measurement target portion Mp, which is a portion of the living body Ob farther inside than the epidermis, such as the dermis, can be held at a defined distance from the front surface 10a of the target placement unit 10.

Further, the target placement unit 10 is disposed so that the laser beam L1 emitted from the light emission unit 20 is incident on a rear surface 10d, and at an angle relative to the light emission unit 20 so that an incident angle θ is defined for an optical axis L1 on an incident side of the front surface 10a. Here, the incident angle θ indicates an angle of the optical axis L1 with respect to the normal to the front surface 10a of the target placement unit 10 on which the living body Ob is placed.

Figure 2A:
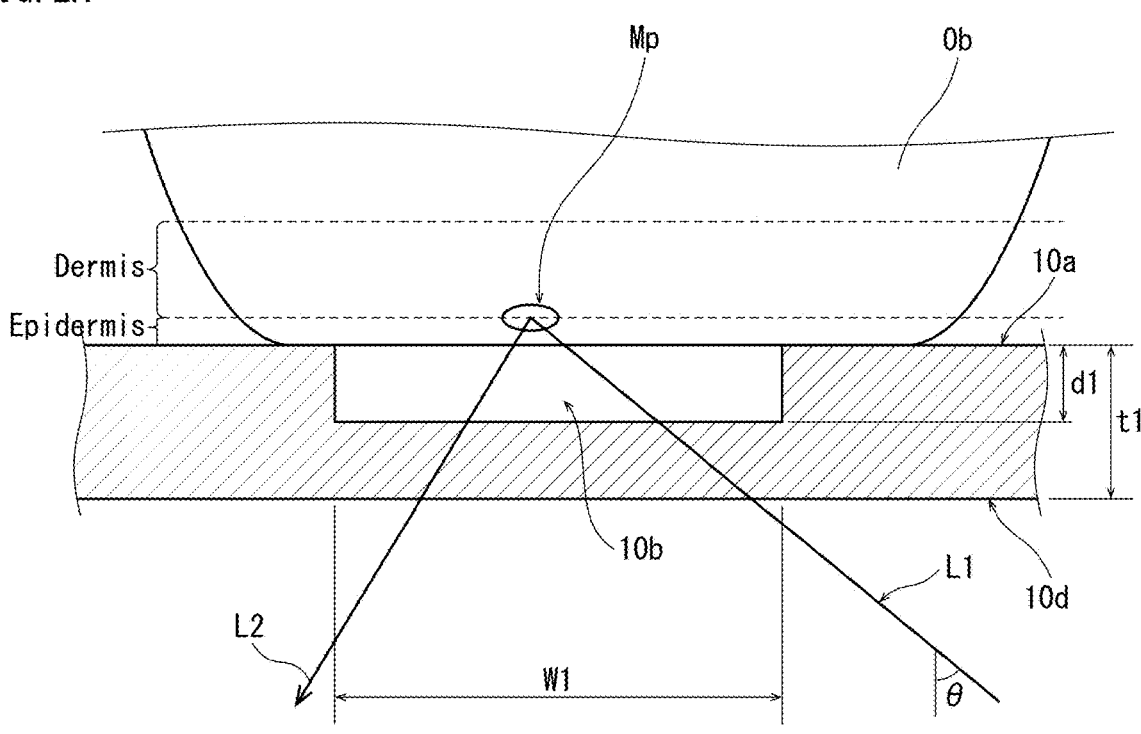
FIG. 2A, 2B are enlarged cross-section diagrams of portion A in FIG. 1.
Figure 2B:
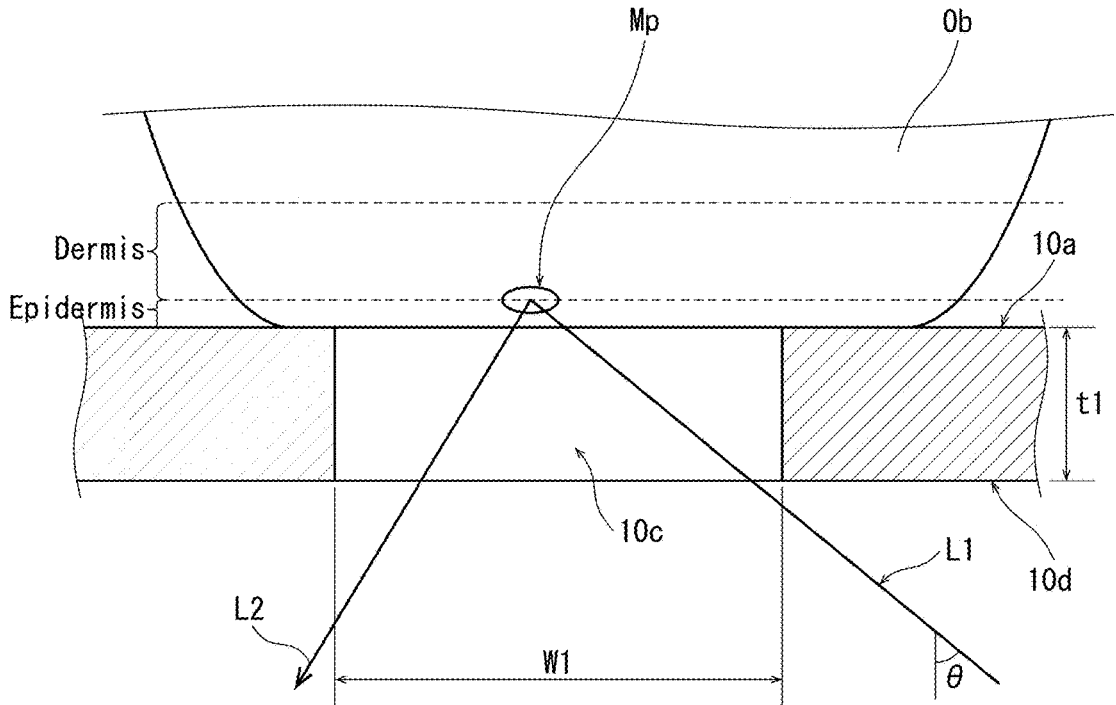

FIG. 2A, 2B are enlarged cross-section diagrams of a portion A in FIG. 1. The enlarged diagrams illustrate a portion where the measurement target portion Mp of the living body Ob is brought into contact with the target placement portion 10. As illustrated in FIG. 2A, the front surface 10a of the target placement unit 10 may be formed with a concave portion 10b such that a there is a gap between the living body Ob. In such a case, the laser beam L1 emitted from the light emission unit 20 is transmitted through a bottom surface of the concave portion 10b in the target placement unit 10 to irradiate the surface of the living body Ob. The target placement unit 10 is not an opening, and therefore it is possible to prevent dust, dirt, water vapor, and the like from entering the environment in which the optical system such as the light emission unit 20 exists, and therefore the target placement unit 10 has a dust-proofing function.

By providing the concave portion 10b, an air layer is formed between the front surface 10a of the target placement unit 10 and the living body Ob, and when compared to a case where the target placement unit 10 is in full contact with the living body Ob, total reflection in the surface of the living body Ob may be suppressed. Further, by providing the concave portion 10b, the living body Ob can more easily be brought into close contact with portions of the front surface 10a of the target placement unit 10 other than the concave portion 10b. According to the present embodiment, as an example, thickness of the target placement unit 10 is approximately 500 μm, width of the concave portion 10b is approximately 700 μm, and thickness of the air layer in the concave portion 10b is approximately 400 μm.

Alternatively, as illustrated in FIG. 2B, the front surface 10a of the target placement unit 10 may have an opening 10c in an area of contact with the surface of the living body Ob. Due to the opening 10c, which is a hole through the target placement unit 10, the laser beam L1 emitted from the light emission unit 20 irradiates the surface of the living body Ob through the opening 10c.

By providing the opening 10c, an air layer is formed in a portion where the front surface 10a of the target placement unit 10 and the living body Ob come into contact, and compared to a case where the target placement unit 10 is in full contact with the living body Ob, total reflection in the surface of the living body Ob can be suppressed. Further, by providing the opening 10c, the living body Ob can be more easily brought into close contact with the front surface 10a of the target placement unit 10 around the opening 10c in the front surface 10a. According to the present embodiment, as an example, thickness of the target placement unit 10 is 500 μm and width of the opening 10b is 700 μm.

(Light Emission Unit 20)

The light emission unit 20 is a light source that irradiates a living body with a laser beam of a specific wavelength directed at the measurement target portion Mp. In the substance-in-blood concentration measurement device 1, the light emission unit 20 is disposed facing the rear surface 10d side opposite the body placement surface 10a side of the target placement unit 10, and therefore a laser beam is emitted from the rear surface 10d side towards the measurement target portion Mp of the living body Ob on the body placement surface (front surface 10a) of the target placement unit 10.

Figure 3:
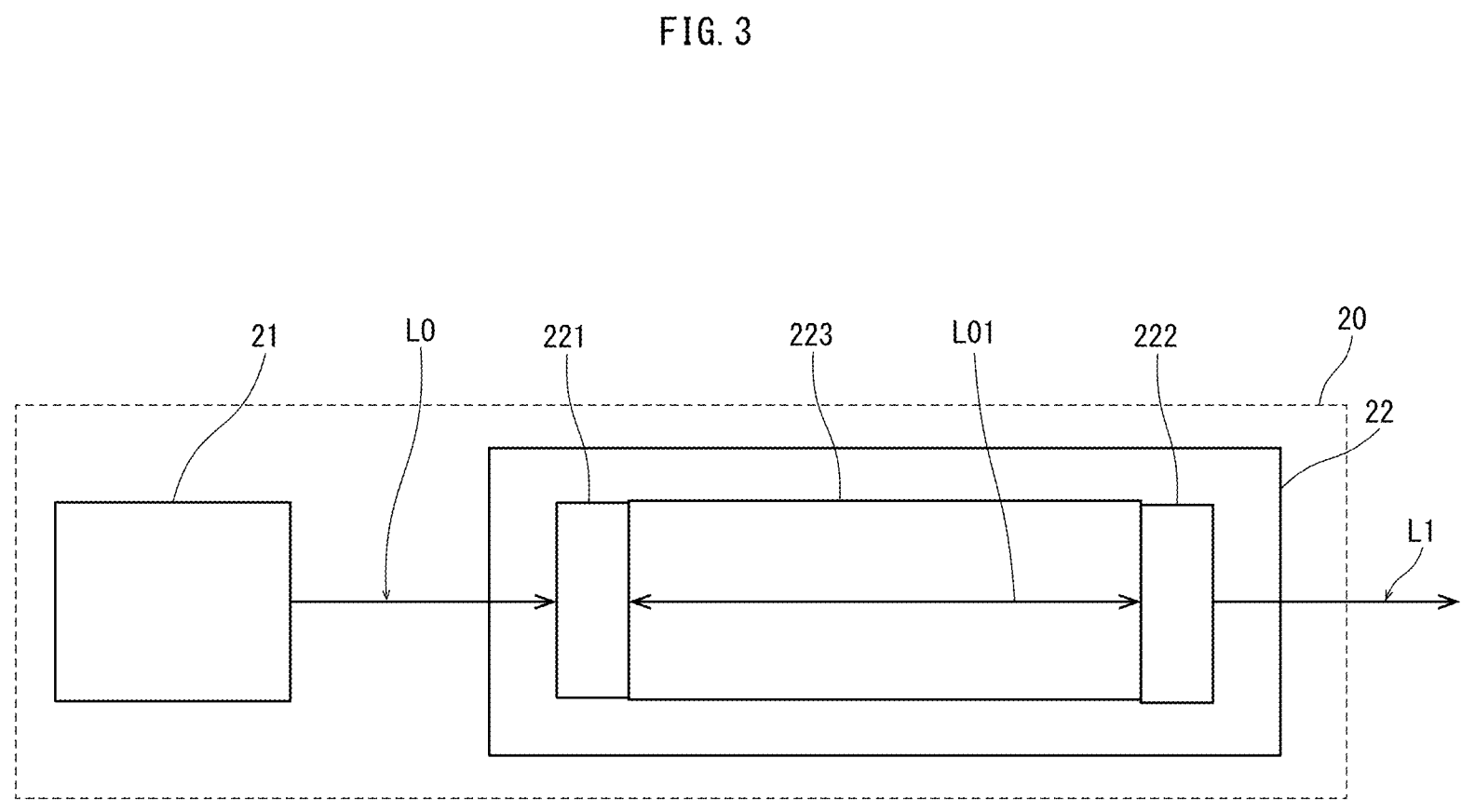

FIG. 3 is a schematic diagram illustrating structure of the light emission unit 20 in the substance-in-blood concentration measurement device 1. As illustrated in FIG. 3, the light emission unit 20 includes a light source 21 that emits oscillating pump light L0 having a shorter wavelength than pulsed mid-infrared light, and an optical parametric oscillator (OPO) 22 that converts to a longer wavelength, amplifies, and emits as the laser beam L1. In the OPO 22, when the pump light L0 is incident on a nonlinear optical crystal incorporated therein, light of two different wavelengths is oscillated to generate short-wavelength signal light and long-wavelength idler light The light emission unit 20 outputs the idler light as the laser beam L1 at a later stage, to be used for measuring blood sugar level. The OPO 22 may have the structure described in a known reference, for example JP 2010-281891. Here, as a wavelength at which the OPO 22 oscillates, mid-infrared light is used as a wavelength that is more absorbed by glucose than the near-infrared light conventionally used, and according to the present embodiment, 9.26 μm is used. Compared to near-infrared light conventionally used to measure blood sugar levels, mid-infrared light has lower transmittance into the living body, and therefore only the skin region is measured, obtaining an effect of being less influenced by other biological components deeper than the epidermis. Further, an effect is achieved that measurement is less adversely affected by overtones and combination tones of reference oscillation The light source 21 may include a Q-switched Nd:YAG laser (oscillation wavelength 1.064 μm) or a Q-switched Yb:YAG laser (oscillation wavelength 1.030 μm). Accordingly, the pump light L0 having a wavelength shorter than that of mid-infrared light is oscillated in pulses. The pump light L0 may have, for example, a pulse width of approximately 8 ns and a frequency of 10 Hz or higher. Further, according to a Q-switched Nd:YAG laser or Yb:YAG laser, the light source 21 can be simplified and miniaturized due to operating as a passive Q-switch that switches passively using a saturable absorber.

As illustrated in FIG. 3, the OPO 22 includes an incident-side semi-transmissive mirror 221, an output-side semi-transmissive mirror 222, and a nonlinear optical crystal 223. The OPO 22 is an optical resonator in which the incident-side semi-transmissive mirror 221 and the output-side semi-transmissive mirror 222 face each other across a the nonlinear optical crystal 223. Light L01 transmitted through the incident-side semi-transmissive mirror 221 enters the nonlinear optical crystal 223 and is converted into light having a wavelength of 9.26 μm determined by the nonlinear optical crystal 223 and undergoes optical parametrical amplification between the incident-side semi-transmissive mirror 221 and the output-side semi-transmissive mirror 222. The amplified light is transmitted through the output-side semi-transmissive mirror 222 and is output as the laser beam L1.

In the nonlinear optical crystal 223, AgGaS suitable for wavelength conversion is used under phase matching conditions. Wavelength of the oscillated laser beam L1 can be adjusted by adjusting the type and matching conditions of the nonlinear optical crystal 223. GaSe, $ZnGeP_2$, $CdSiP_2$, $LiInS_2$, $LiGaSe_2$, $LiInSe_2$, $LiGaTe_2$, and the like may be used for the nonlinear optical crystal 223. The laser beam L1 emitted from the OPO 22 has a repetition frequency corresponding to the pump light L0, for example a pulse width of approximately 8 ns, and a short pulse width can achieve a high intensity peak output from 10 W to 1 kW.

Thus, in the light emission unit 20, by using the light source 21 and the OPO 22, the laser beam L1 is achieved that has from $10^3$ to $10^5$ times the intensity of a conventional light source that obtains a wavelength of 9.26 μm, such as a quantum cascade laser.

According to this structure, blood sugar levels are measurable using mid-infrared light, which has a low transmittance into the living body.

(Condenser Lens 50)

As illustrated in FIG. 1, a condenser lens 50 (hereinafter also referred to as a "second lens") for condensing emitted light onto the measurement target portion Mp of the living body Ob is disposed on an optical path Op1 of the laser beam L1 from the light emission unit 20 to the measurement target portion Mp. In a section of the optical path Op1 from the light emission unit 20 to the rear surface 10*d* of the target placement unit 10 is a structure such that the laser beam L1 propagates through space such as a gas, for example, except where passing through the condenser lens 50. The condenser lens 50 has an optical design such that the laser beam L1 emitted from the light emission unit 20 is focused to a depth corresponding to a part of the living body inwards of the epidermis, such as the dermis, corresponding to the measurement target portion Mp of the living body Ob, which is separated by a defined distance from the front surface 10*a* of the target placement unit 10. The incident angle θ of the laser beam L1 on the measurement target portion Mp is determined by the angle of the light emission unit 20 with respect to the front surface 10*a* of the target placement unit 10 and the refraction angle of the laser beam L1 incident on the target placement unit 10. According to the present embodiment, the incident angle θ may be, for example, 45 degrees or more, or may be from 60 degrees to 70 degrees.

A beam splitter (not shown) including a semi-transmissive mirror may be disposed between the light emission unit 20 and the condenser lens 50 to split a portion of the laser beam L1 as a reference signal, and a monitoring device (not shown) may be used to detect changes in intensity of the laser beam L1 for use in normalization processing of the detection signal in the photodetector 30. Output of the photodetector 30 may be compensated based on variation in intensity of the laser beam L1.

The laser beam L1 transmitted through the condenser lens 50 is transmitted through the target placement unit 10 an incident on the living body Ob, transmitted through the epithelial interstitial tissue of the living body and scattered or diffusely reflected as reflected light L2, which is again transmitted through the target placement unit 10 and emitted towards the photodetector 30.

(Imaging Lens 40)

Figure 4:
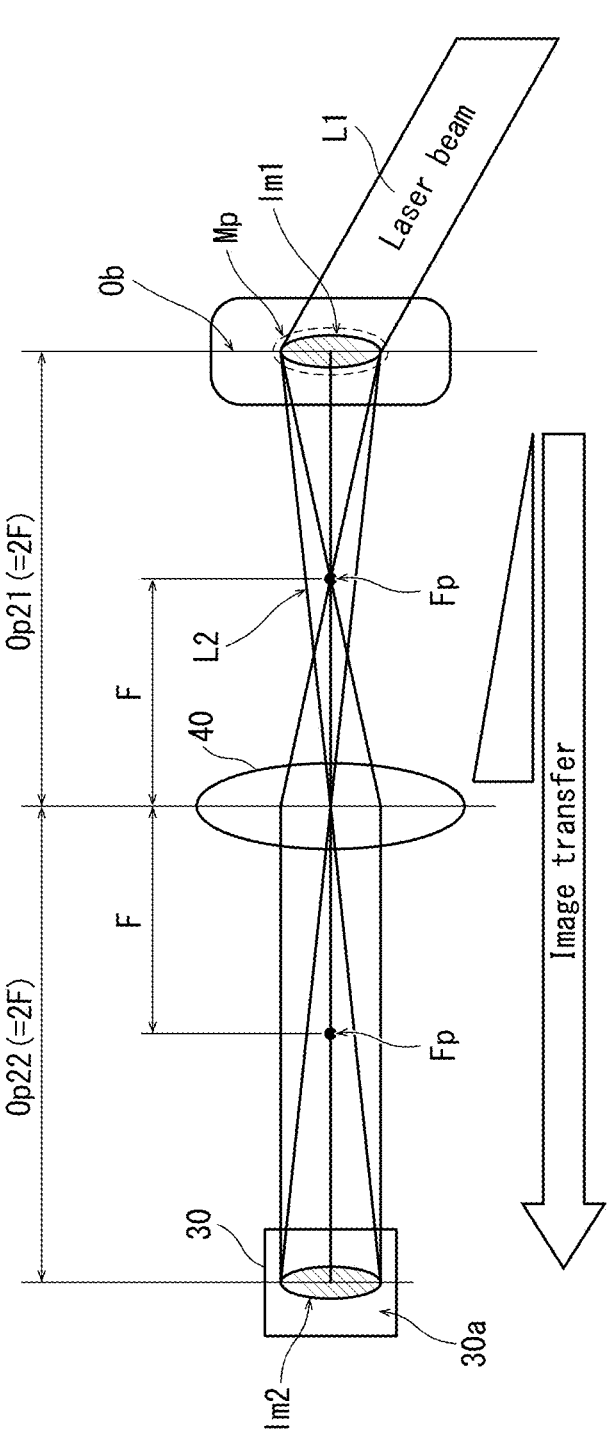
FIG. 4 is a diagram illustrating an overview of a light-reception path in the substance-in-blood concentration measurement device 1.

FIG. 4 is a schematic diagram for explanation of an outline of light-receiving-side optical path in the substance-in-blood concentration measurement device 1, drawn in plan view of the measurement target portion Mp of the living body Ob and a screen 30*a* of the photodetector 30. As illustrated in FIG. 1 and FIG. 4, the imaging lens 40 (hereinafter also referred to as a "first lens") is disposed on an optical path Op2 of the reflected light L2 from the measurement target portion Mp of the living body Ob to the photodetector 30, in order to form an image on the photodetector 30 from the reflected light L2 diffusely reflected at the measurement target portion Mp of the living body Ob. In a section of the optical path Op2 from the rear surface 10*d* of the target placement unit 10 to the photodetector 30 is a structure such that the reflected light L2 propagates through space such as a gas, for example, except where passing through the imaging lens 40.

The imaging lens 40 has an optical design such that an image Im1 in a range corresponding to the measurement target portion Mp of the living body Ob as the diffusely reflected light L2 forms an image Im2 on the screen 30*a* of the photodetector 30 due to the imaging lens 40.

According to the present embodiment, a distance Op21 between a center of the imaging lens 40 to the measurement target portion Mp of the living body Ob and a distance Op22 between the screen 30a of the photodetector 30 and the center of the imaging lens 40 are equal, and the image Im1 of a depth corresponding to a portion of the living body inwards of the epidermis, such as the dermis (which hereinafter may also be referred to as an "inner portion of the living body"), which corresponds to the measurement target portion Mp of the living body Ob irradiated with mid-infrared light, is transferred as the image Im2 of equivalent size onto the screen 30a of the photoconductor 30. When a focal length F is a focal point Fp of the imaging lens 40, the distance Op21 and the distance Op22 may each be equal to 2 F.

However, lengths of the distance Op21 and the distance Op22 are not limited to the above, and the imaging lens 40 may be set to achieve magnifications of the distance Op21 and the distance Op22 such that the image Im1 of the target placement unit 10 irradiated by mid-infrared light fits precisely in the screen 30a of the photodetector 30.

An incident angle of the reflected light L2 to the imaging lens 40 is determined by an angle of the imaging lens 40 with respect to the front surface 10a of the target placement unit 10 and a refraction angle of the reflected light L2 emitted from the target placement unit 10. According to the present embodiment, the incident angle may be, for example, from 0 degrees to 40 degrees, or more preferably from 20 degrees to 30 degrees.

(Photodetector 30)

The photodetector 30 is a mid-infrared sensor that receives light reflected from the measurement target portion Mp irradiated by the laser beam L1, and detects intensity of the reflected light In the substance-in-blood concentration measurement device 1, the photodetector 30 is disposed facing the rear surface 10d side of the living body placement surface 10a of the target placement unit 10, and receives light reflected from the measurement target portion Mp of the living body Ob on the body placement surface (front surface) 10a, from the rear surface 10d side of the target placement unit 10. The photodetector 30 outputs an electrical signal corresponding to intensity of received reflected light The photodetector 30 may be, for example, a single-element infrared sensor that outputs the intensity of the reflected light as a one-dimensional voltage value.

In the substance-in-blood concentration measurement device 1, due to the light emission unit 20 increasing intensity of the laser beam L1, the photodetector 30 may receive sufficiently high intensity reflected light relative to background light due to the imaging by the imaging lens 40 on the photodetector 30 of the light reflected from the measurement target portion Mp, thereby realizing a high signal-to-noise (S/N) ratio and enabling highly accurate measurement In this way, since the laser beam L1 and the reflected light L2 are monochromatic and high intensity, the only processing required for the photodetector 30 is detection of light intensity and there is no need to execute spectrum analysis or multivariate analysis based on wavelength sweeping, as in a photo-acousto-optic method using a quantum cascade laser. Therefore, there is some relaxation in the amount of accuracy required for detection, and an easily used method such as an electronic cooling method may be used.

The photodetector 30 may use, for example, an HgCdTe infrared detector cooled with liquid nitrogen. By cooling to about 77 K with liquid nitrogen, light intensity of the reflected light L2 is detectable with a higher S/N ratio.

(Controller 60)

The controller 60 is electrically connected to the light emission unit 20 and the photodetector 30, drives the light source 21 of the light emission unit 20 to oscillate the pulsed pump light L0, and detects light intensity of the reflected light L2 based on an output signal from the photodetector 30 to calculate glucose concentration in the measurement target portion Mp of the living body Ob.

Alternatively, the controller 60 may receive output from the monitoring photodetector, and as described above, even if intensity of the laser beam L1 emitted from the light emission unit 20 fluctuates, may calculate glucose concentration by normalizing the output of the photodetector 30 to compensate for the influence of laser beam L1 intensity fluctuations by using output from the monitoring photodetector.

<Evaluation Testing>

Performance evaluation testing was performed using the substance-in-blood concentration measurement device 1 according to an embodiment. The following describes the results.

(Test 1: Evaluation of Embodiment of Substance-in-Blood Concentration Measurement Device 1 and Reference Example)

[Test Device, Conditions]

As the embodiment, the substance-in-blood concentration measurement device 1 according to the embodiment illustrated in FIG. 1 was used. Device conditions of the substance-in-blood concentration measurement device 1 were as follows.

(1) The target placement unit 10 was placed horizontally, a mid-infrared laser beam upwards from the light emission unit 20 at an angle of 24.5 degrees from the horizontal to irradiate a marked measurement position from a bottom portion of the target placement unit 10. At this time, an irradiation range of the laser beam L1 was reduced to a size corresponding to the measurement position by the condenser lens 50.

(2) A subject's fingertip was placed on the front surface 10a on the upper side of the target placement unit 10, so the incident angle was 65.5 degrees.

(3) An image of the measurement target portion Mp of the living body Ob irradiated by mid-infrared light was transferred by the imaging lens 40 disposed below the target placement unit 10 to be formed on the photodetector 30. When the focal length of the imaging lens is F, positional relationships were set such that the distance between the screen 30a of the photodetector 30 and the center of the image lens 40 and the distance between the center of the imaging lens 40 and the measurement target portion Mp of the living body Ob were both 2 F, and the image Im1 at the depth corresponding to the portion of the living body inwards of the epidermis corresponding to the measurement target portion Mp was transferred to the photodetector 30 with an equivalent size.

(4) The angle of the optical path Op2 between the photodetector 30 and the imaging lens 40 was set at an angle inclined 25 degrees clockwise from the vertical direction of the target placement unit 10.

Further, as the reference example, the conventional substance-in-blood concentration measurement device 1X disclosed in Patent Literature 1 and illustrated in FIG. 17 was used.

[Testing Method]

(1) The subject ingested an aqueous solution containing 40 g of glucose (time of ingestion was defined as measurement start time: 0 minutes), the subject's fingertip was placed on the front surface 10*a* of the upper side of the target placement unit 10, and optical measurement was performed continuously by both the embodiment and the reference example. In the optical measurement, a mid-infrared laser beam was emitted for a certain period of time, and blood sugar level was calculated from a change in intensity of the mid-infrared light when the living body was irradiated.

(2) In parallel with the optical measurement, self-monitoring of blood glucose (SMBG) was performed by the subject sampling their own blood.

(3) Optical measurement and sampling by SMBG were repeated at fixed time intervals (10 to 15 minutes), and measured values were plotted for each elapsed time interval. [Test Results]

First is a description of the results of the conventional device 1X according to the reference example.

FIG. 5A, 5B, 5C, 5D are diagrams comparing changes over time in glucose concentration measured by the photodetector of the conventional device 1X and changes over time in glucose concentration measured by a conventional invasive measurement device. FIG. 6A, 6B, 6C, 6D are diagrams illustrating correlation between glucose concentration measurements by the photodetector and glucose concentration measurements by the invasive measurement device of FIG. 5A, 5B, 5C, 5D.

FIG. 5A, 5B, 5C, 5D illustrate results of tests conducted on the same subject on different test days.

After ingestion of the aqueous solution, blood sugar level according to SMBG rises over time then falls.

Figure 5B:
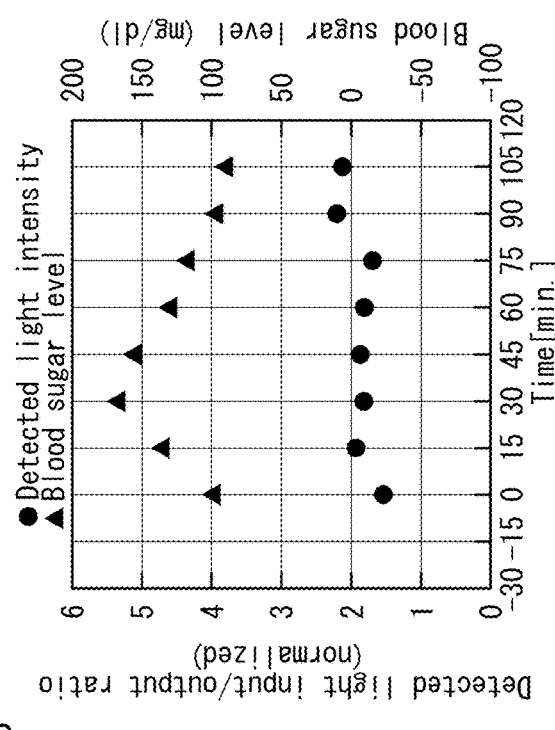
FIG. 5A, 5B, 5C, 5D are diagrams comparing changes over time in glucose concentration measured by a photodetector of a conventional noninvasive substance-in-blood concentration measurement device 1X and changes over time in glucose concentration measured by a conventional invasive measurement device.
Figure 5D:
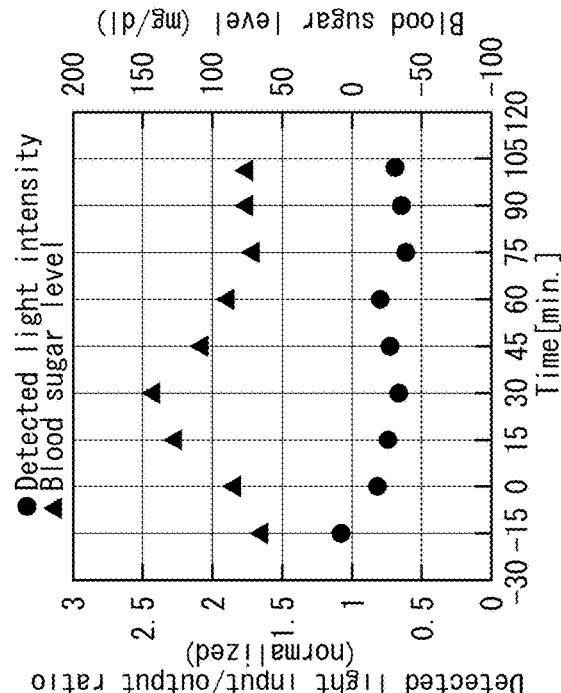
Figure 5A:
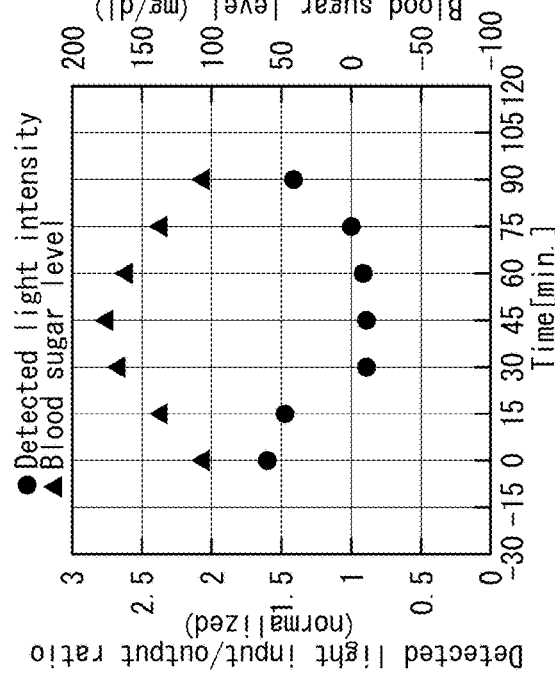

In FIG. 5A, light intensity detected by optical measurement decreases then increases over time after ingestion of the aqueous solution due to light absorption changes corresponding to blood glucose concentration, and a negative correlation with blood sugar level measurement results according to SMBG was confirmed (FIG. 6A).

Figure 5C:
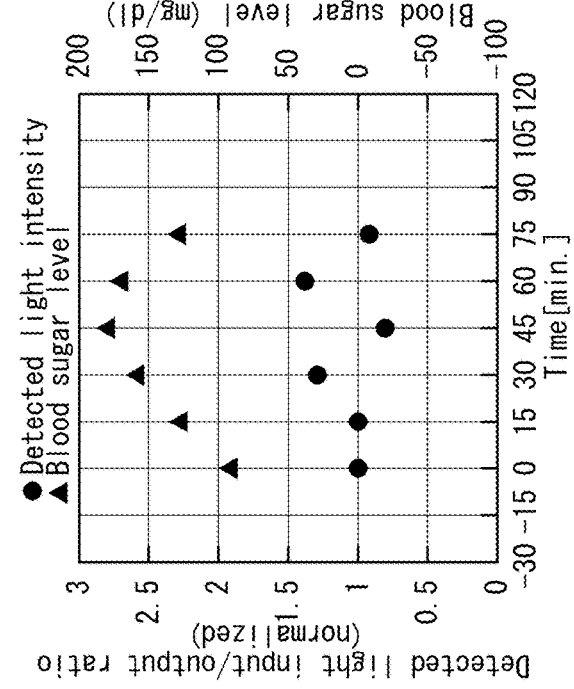

However, in the results illustrated in FIG. 5B and FIG. 5C, which were obtained on different test days, no clear tendency of decreasing then increasing over time after ingestion of the aqueous solution was observed, and the results showed a low correlation with blood sugar measurement results according to SMBG (FIG. 6B, 6C). Further, in the results illustrated in FIG. 5D, after ingestion of the aqueous solution, a tendency of decreasing then increasing over time was observed, but the negative correlation was small and the reaction was extremely small (FIG. 6D).

As described above, the conventional device 1X according to the reference example sometimes failed to take normal measurements even under the same conditions, depending on the day of the test.

Figure 7A:
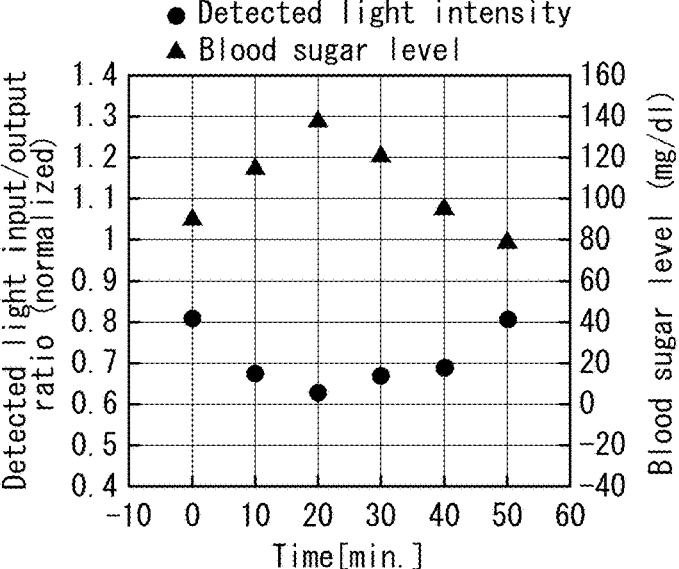
FIG. 7A, 7B, 7C are diagrams comparing changes over time in glucose concentration measured by a photodetector of the substance-in-blood concentration measurement device 1 and changes over time in glucose concentration measured by an invasive measurement device.
Figure 7B:
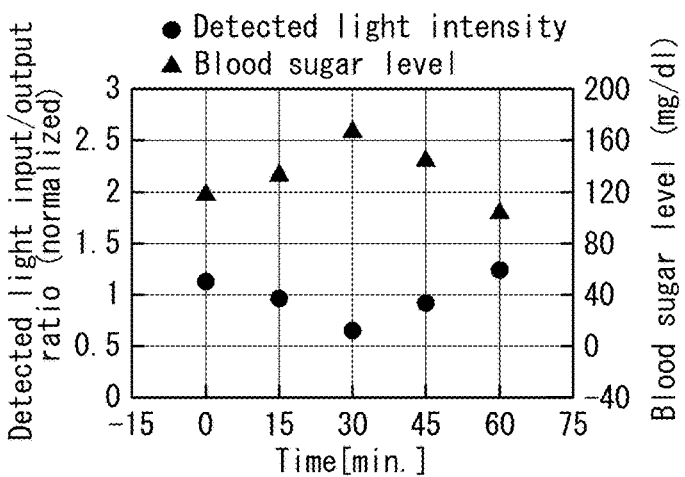
Figure 7C:
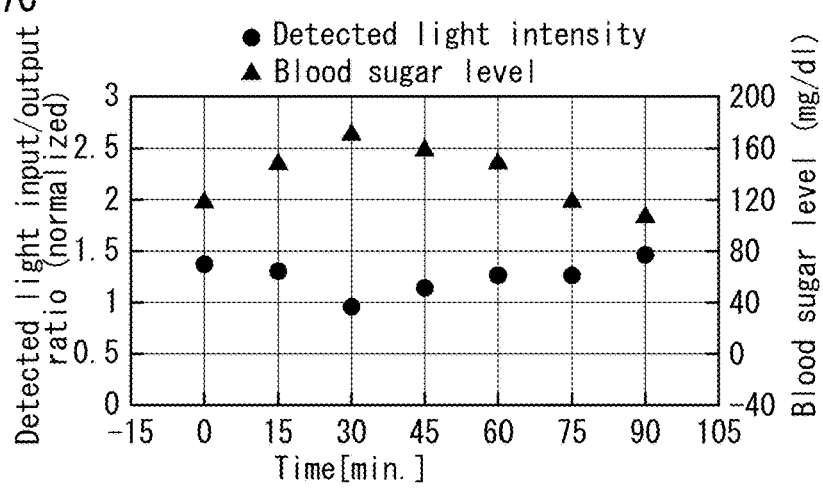
Figure 8A:
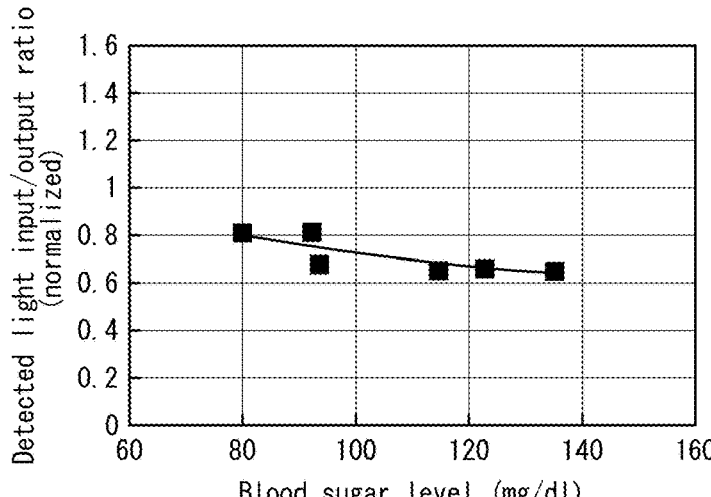
FIG. 8A, 8B, 8C are diagrams illustrating correlation between glucose concentration measurements by the photodetector and glucose concentration measurements by the invasive blood glucose concentration measurement device of FIG. 7A, 7B, 7C.
Figure 8B:
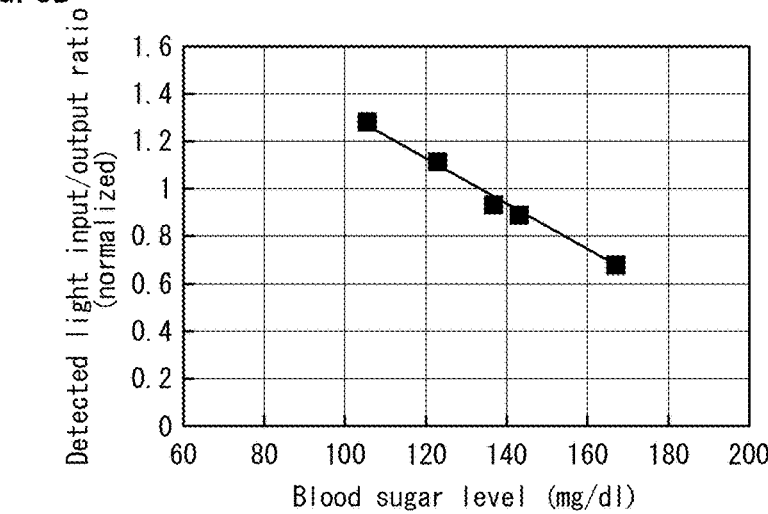
Figure 8C:
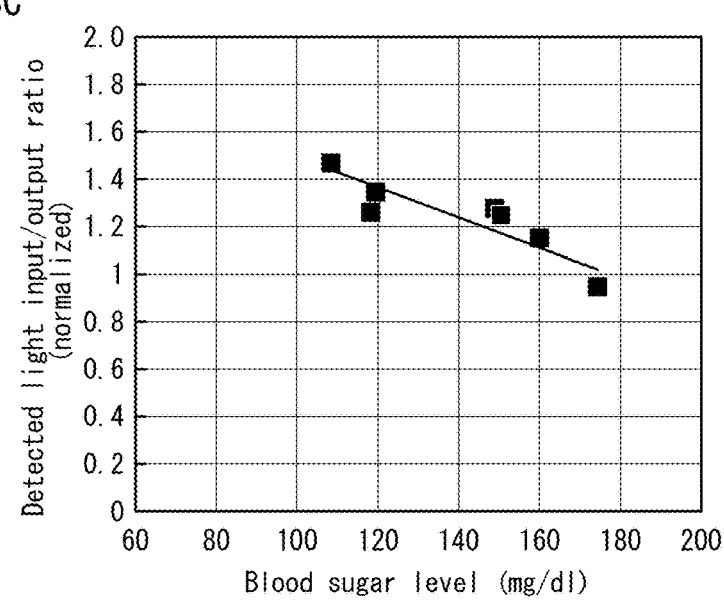

Next is a description of results obtained by the substance-in-blood concentration measurement device 1 according to the embodiment FIG. 7A, 7B, 7C are diagrams comparing changes over time in glucose concentration measured by the photodetector of the substance-in-blood concentration measurement device 1 and changes over time in glucose concentration measured by an invasive measurement device. FIG. 8A, 8B, 8C are diagrams illustrating correlation between glucose concentration measurements by the photodetector and glucose concentration measurements by the invasive blood glucose concentration measurement device of FIG. 7A, 7B, 7C.

FIG. 7A, 7B, 7C illustrate results of tests conducted on the same subject on different test days.

FIG. 7A, 7B, 7C show that light intensity detected by measurement decreases then increases over time after ingestion of the aqueous solution, due to light absorption changes corresponding to blood glucose concentration, and when compared to the blood sugar level measurement results by SMBG, a strong negative correlation was confirmed in FIG. 8B and a negative correlation was confirmed in FIG. 8A, 8C.

From the above results, it was confirmed that the substance-in-blood concentration measurement device 1 according to the embodiment, in repeated experiments conducted on different days, obtained more stable measurement results with stronger correlation with blood sugar level measurement by SMBG than the reference example.

(Test 2: Evaluation Changing Light Reception Angle Φ of Photodetector)

[Test Device, Conditions]

Optical measurements were performed changing the angle Φ of the optical path on the light receiving side.

Figure 9:
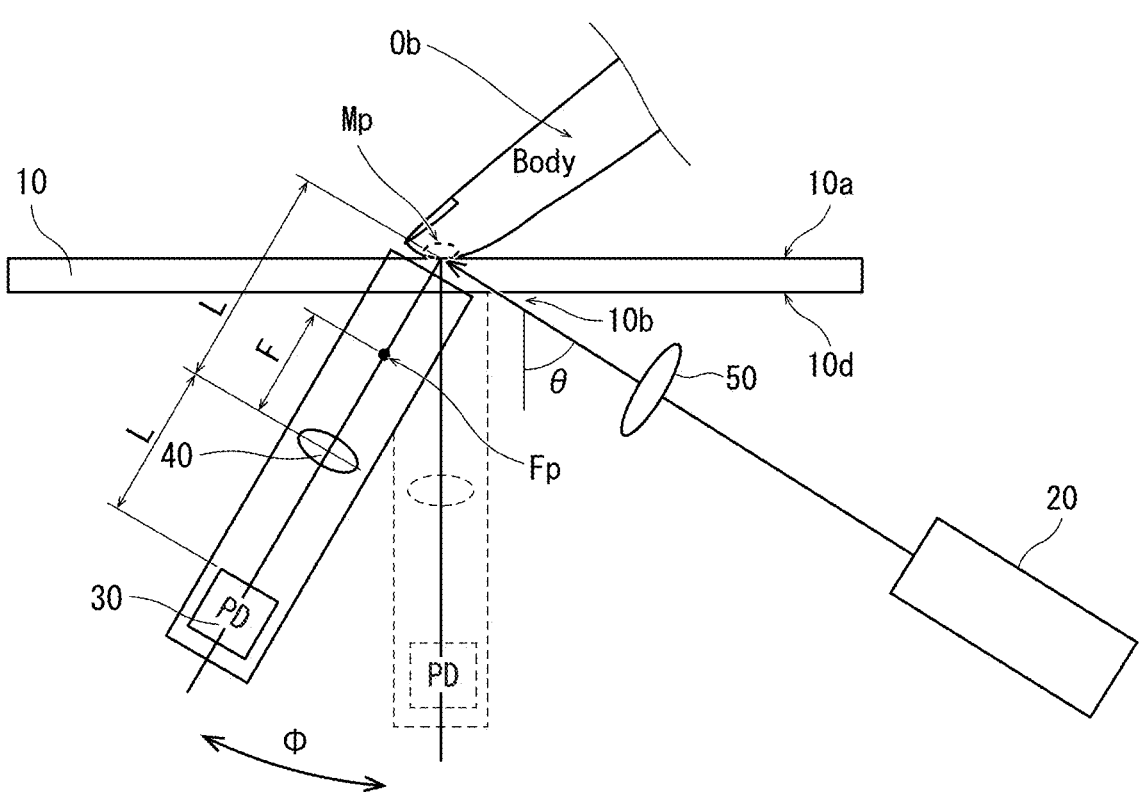
FIG. 9 is a schematic diagram of an experimental apparatus measuring measured values of glucose concentration by a photodetector while changing a light reception angle of the substance-in-blood concentration measurement device 1.

FIG. 9 is a schematic diagram of an experimental device for measuring glucose concentration measured by the photodetector when changing angle and length of the optical path on the light reception side of the substance-in-blood concentration measurement device 1. Using the substance-in-blood concentration measurement device 1 of the embodiment used in Test 1, optical measurement was performed with different values for the angle Φ of the optical path Op2 between the photodetector 30 and the imaging lens 40, from 0 degrees to 40 degrees clockwise from the reference of the normal to the surface of the target placement unit 10 on which the living body Ob is placed (vertical direction in FIG. 9). Other device conditions and test methods were the same as in Test 1.

[Test Results]

Figure 10A:
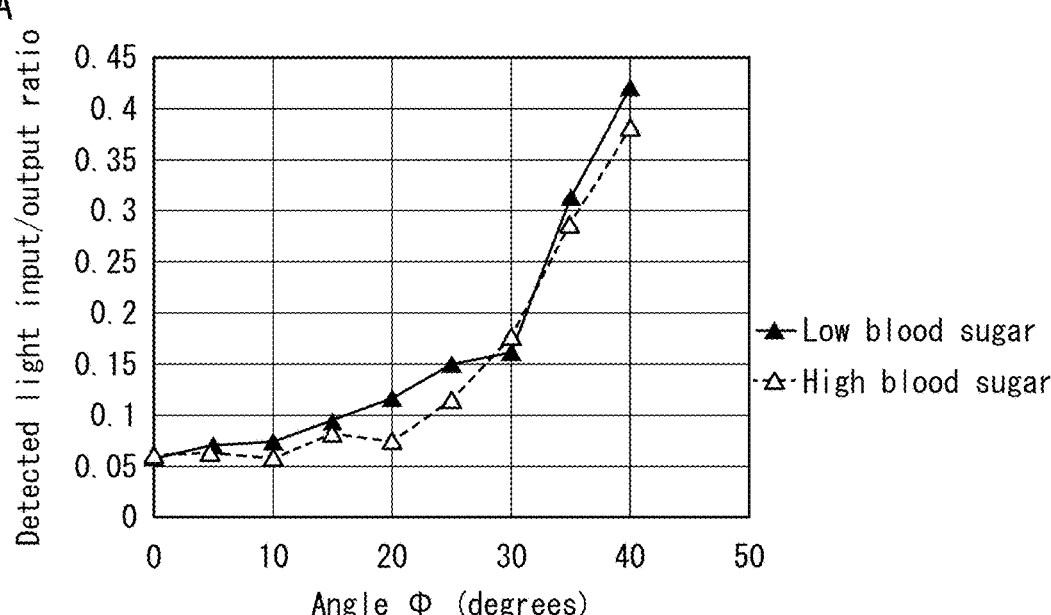
FIG. 10A, 10B are diagrams illustrating changes in measurements of glucose concentration when the light reception angle of the photodetector of the substance-in-blood concentration measurement device 1 is changed.
Figure 10B:
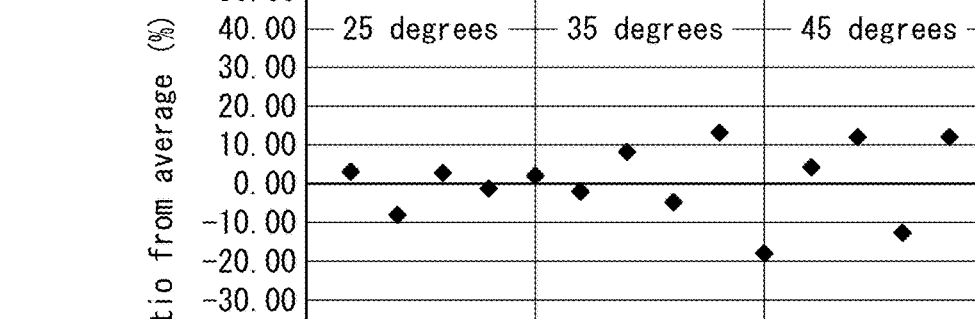

FIG. 10A, 10B are diagrams illustrating changes in glucose concentration measured at different light reception angles of the photodetector in the substance-in-blood concentration measurement device 1, where FIG. 10A illustrates a relationship between the angle Φ and input/output ratios of detected light in optical measurements, and FIG. 10B illustrates experimental results showing variation in measurement results for each number of measurements at each angle Φ.

From FIG. 10A it can be seen that absorption was observed for values of the angle Φ from 0 degrees to 40 degrees, and the greatest absorption was observed from 20 degrees to 30 degrees. Further, it was confirmed that the signal increased when the angle Φ exceeded 40 degrees. As the angle Φ increases beyond 40 degrees, the angle Φ becomes even closer to an angle of regular reflection for incident light, which is considered unsuitable for use in optical measurement. Further, it is preferable from the point of view of measurement accuracy that the input/output ratio is 0.2 or less, and therefore the angle Φ is more preferably 30 degrees or less. Further, an input/output ratio of less than 0.1 is not desirable in terms of S/N ratio, and therefore the angle Φ is more preferably 20 degrees or more.

Further, variation was small when the angle Φ was 0 degrees, as illustrated in FIG. 10B, the smallest variation was observed when the angle Φ was 25 degrees, and the largest variation was observed when the angle Φ was 45 degrees. This is thought to be because when the angle Φ is 45 degrees or more, this approaches the angle of regular reflection of incident light.

Further, when the angle Φ is 45 degrees or more, measurement becomes difficult in terms of device structure. In a range where the angle Φ is less than 20 degrees, the light receiving side of the optical system and the light emitting side of the optical system are close to each other, and therefore the optical system layout of the substance-in-blood concentration measurement device 1 becomes difficult From the above results, it is considered that the angle Φ of the light reception optical path is preferably from 0 degrees to 40 degrees, and more preferably from 20 degrees to 30 degrees. Further, in order to suppress the influence of regular reflection of incident light, the incident angle of the laser beam is preferably different from the emission angle to the photodetector.

(Test 3: Evaluation Changing Optical Path Length L on Light Receiving Side)

[Test Device, Conditions]

Optical measurements were performed changing the optical path length L on the light receiving side.

Using the substance-in-blood concentration measurement device 1 of the embodiment used in Test 1, optical measurements were performed under conditions where the distance L between the screen 30a of the photodetector 30 and the center of the imaging lens 40 and the distance L between the center of the imaging lens 40 and the measurement target portion Mp of the living body Ob (hereinafter also referred to as the "optical path length L") were changed relative to the focal distance F of the imaging lens, to the values 2 F−0.5 mm, 2 F mm, and 2 F+0.5 mm. Other device conditions and test methods were the same as in Test 1.

[Test Results]

Figure 11A:
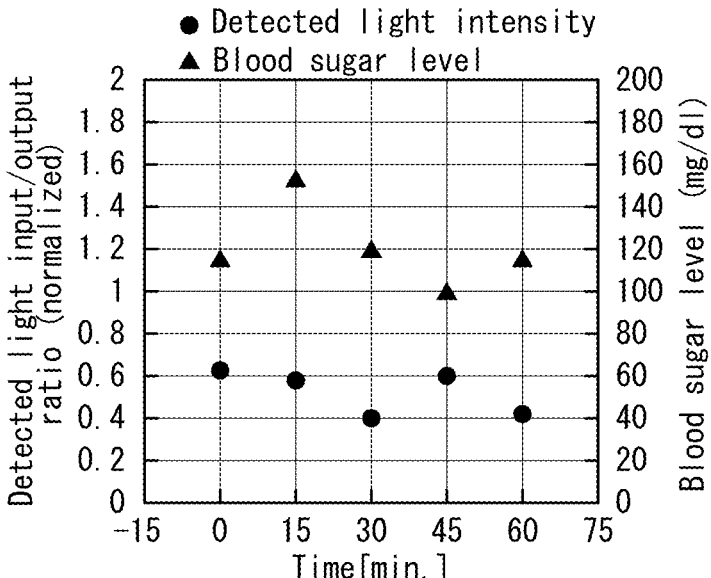
FIG. 11A, 11B are diagrams comparing changes over time in glucose concentration measured by a photodetector when length of a light reception optical path is changed in the substance-in-blood concentration measurement device 1 and changes over time in glucose concentration measured by an invasive measurement device.
Figure 11B:
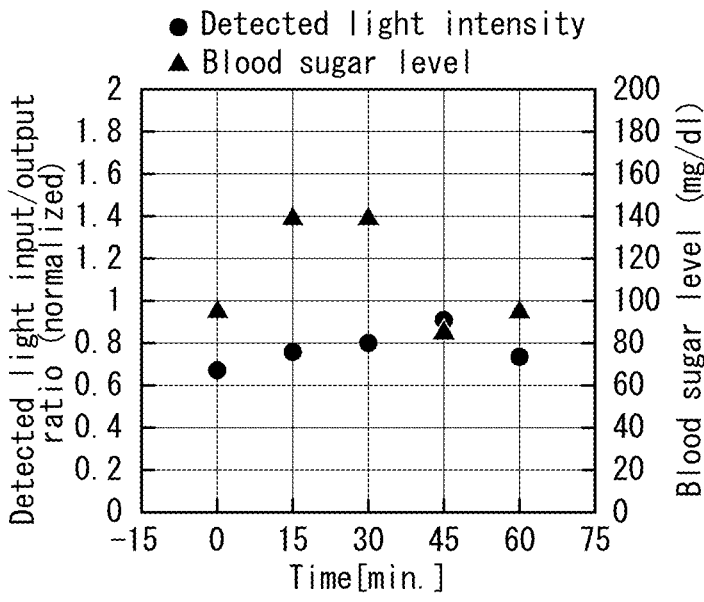

FIG. 11A, 11B are diagrams comparing changes over time in glucose concentration measured by the photodetector when length of the light reception optical path is changed in the substance-in-blood concentration measurement device 1 and changes over time in glucose concentration measured by an invasive measurement device.

FIG. 7A, 11A, 11B illustrate test results under the conditions that the optical path length L is 2 F mm, 2 F−0.5 mm, and 2 F+0.5 mm, respectively.

Under the condition that the optical path length L is 2 F mm, detected light intensity measurements, as described above in reference to FIG. 7A, decreased then increased over time after ingestion of the aqueous solution due to light absorption changes accompanying changes in blood glucose concentration. When compared to the results of blood sugar level measurement by SMBG, a strong negative correlation was confirmed, as illustrated in FIG. 8A.

Figure 12A:
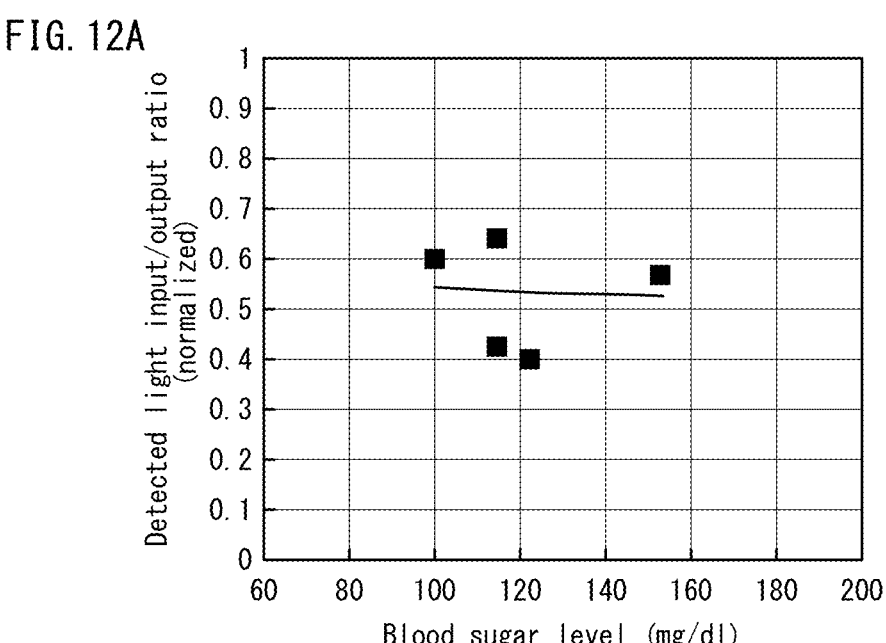
FIG. 12A, 12B are diagrams illustrating correlation between glucose concentration measurements by the photodetector and glucose concentration measurements by the invasive measurement device of FIG. 11A, 11B.
Figure 12B:
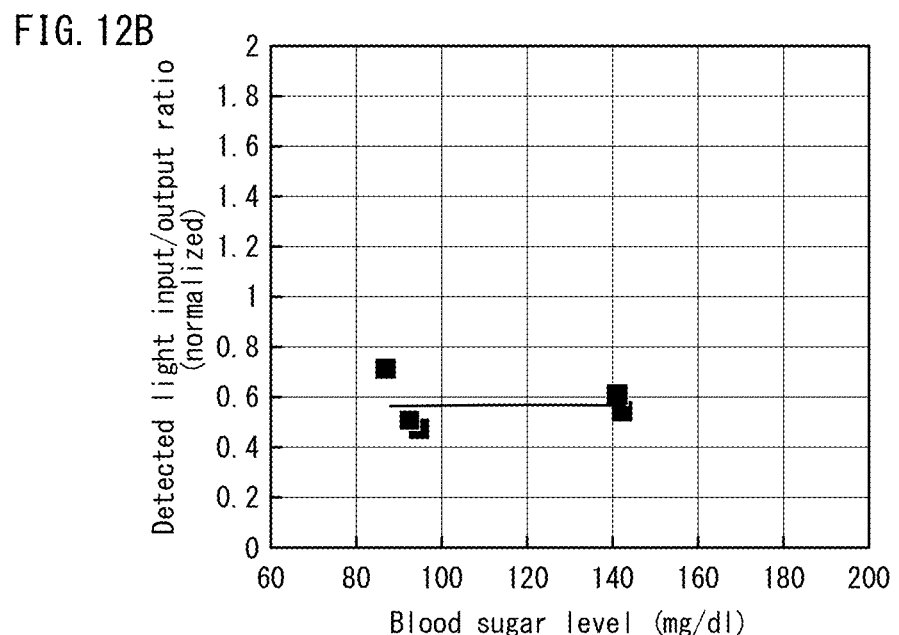

On the other hand, when the optical path length L was 2 F−0.5 mm or 2 F+0.5 mm, detected light intensity measurements, as shown in FIG. 11A, 11B, did not show a tendency to decrease then increase over time after ingestion of the aqueous solution due to light absorption changes accompanying changes in blood glucose concentration. In FIG. 11A, the response due to changes in blood sugar level was extremely small, and in FIG. 11B, almost no response due to changes in blood sugar level was observed. Further, the results showed a low correlation with the measurement results for blood sugar level by SMBG (FIG. 12A, 12B).

From the above results, it is considered preferable that the optical path length L on the light receiving side, that is, the distance L between the screen 30a of the photodetector 30 and the center of the imaging lens 40 and the distance L between the center of the imaging lens 40 and the measurement target portion Mp of the living body Ob, has a length corresponding to the imaging position of the imaging lens 40 (twice the focal length F). It is considered that light reflected from the measurement target portion Mp of the living body Ob, which corresponds to a portion of the living body inwards of the epidermis, forms an image on the screen 30a of the photodetector 30. At this time, a distance between the upper surface 10a of the target placement unit 10 corresponding to the skin surface and the center of the imaging lens 40 was approximately 50 mm, which is shorter than the distance L by approximately 0.8 mm.

<Effects of substance-in-Blood Concentration Measurement Device 1>

As described above, according to the results of Test 1, the conventional device 1X using a waveguide according to the reference example obtained low reproducibility, such that normal measurements could not be performed on different test dates, even under the same conditions.

In contrast, in optical measurements by the substance-in-blood concentration measurement device 1 according to the embodiment, when compared to the conventional device 1X according to the reference example, higher correlation with blood sugar level measurement results by SMBG and higher reproducibility of measurement results were confirmed. The substance-in-blood concentration measurement device 1 is provided with the imaging lens 40 between the measurement target portion Mp and the photodetector 30, and has an optical system with a structure such that the reflected light L2 reflected from the measurement target portion Mp is imaged on the photodetector 30, and this is considered to have enabled optical measurement with high reproducibility.

The reason for this is thought to be that the conventional device 1X using the waveguide according to the reference example cannot separate a component from the skin surface from a component absorbed by blood glucose under the skin, and therefore differences in skin surface condition and small changes in laser irradiation conditions may prevent normal measurement, while in contrast, according to the substance-in-blood concentration measurement device 1 according to an embodiment, signals from under the skin were collected on the optical sensor and therefore the effects of small changes in measurement conditions were reduced, and stable and accurate measurement results were obtained.

The following provides specific description with reference to the drawings.

Figure 13A:
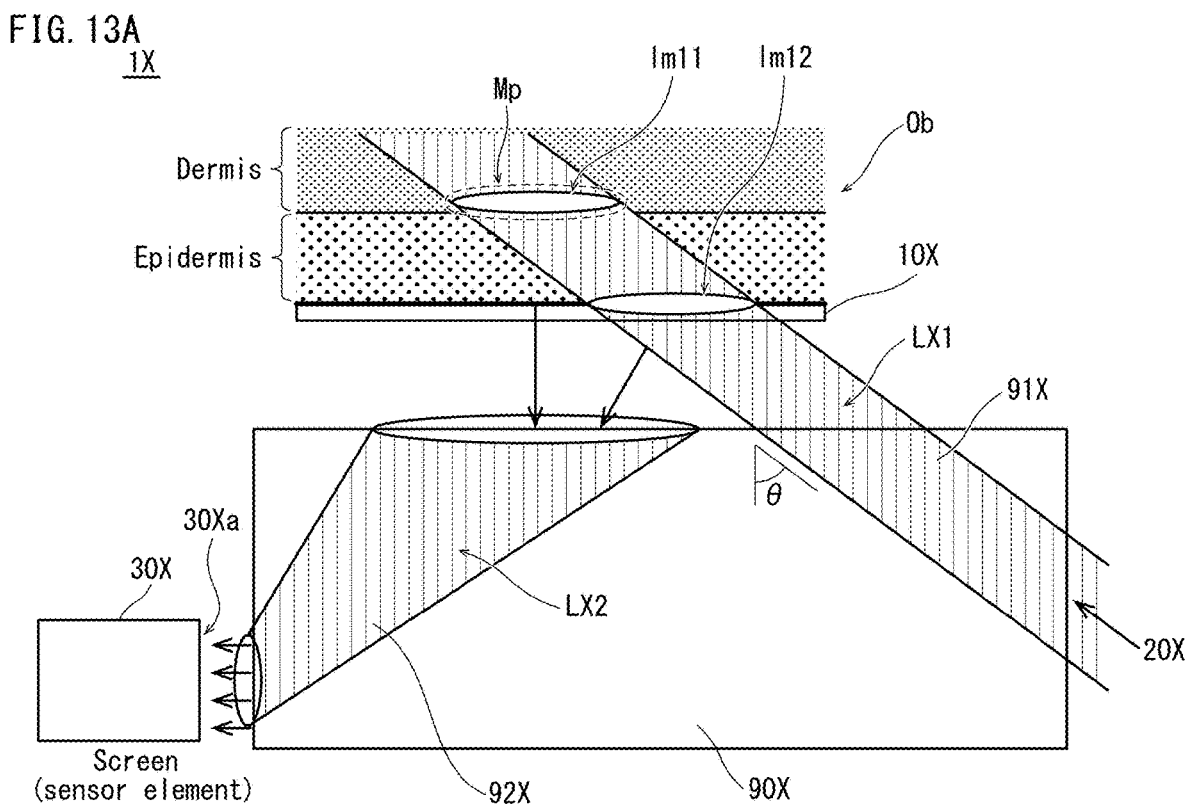
FIG. 13A is a schematic diagram illustrating an optical path from a light emission unit 20X to a photodetector 30X in the conventional substance-in-blood concentration measurement device 1X.

FIG. 13A is a schematic diagram illustrating an optical path from a light emission unit 20X to a photodetector 30X in the conventional substance-in-blood concentration measurement device 1X. As illustrated in FIG. 13A, in the conventional device 1X using a waveguide, a laser beam LX1 emitted from the light emission unit 20X is directed parallel to an incident-side waveguide 91X and is incident on the living body Ob at an incident angle θ along an optical path towards the measurement target portion Mp of the living body Ob. At this time, a reflected light component Im12 from the skin surface is generated in addition to a reflected light component Im11 from a portion of the living body to be measured inwards of the skin surface, where absorption by blood sugar may occur. According to the conventional device 1X using waveguides, these reflected light components Im11, Im12 both enter the output-side waveguide 92X and are guided to a screen 30Xa of the photodetector 30X.

That is, in the conventional device 1X, the reflected light component Im12 from the skin surface and the reflected light component Im11 from the portion of the living body inwards of the skin surface are not separated, and both components mixed together are detected by the photodetector. As a result, it is considered that measurement results include the reflected light component Im12 in addition to the reflected light component Im11 from the portion of the living body inwards of the skin surface that is the measurement target, leading to increased variation factors and low reproducibility.

Figure 13B:
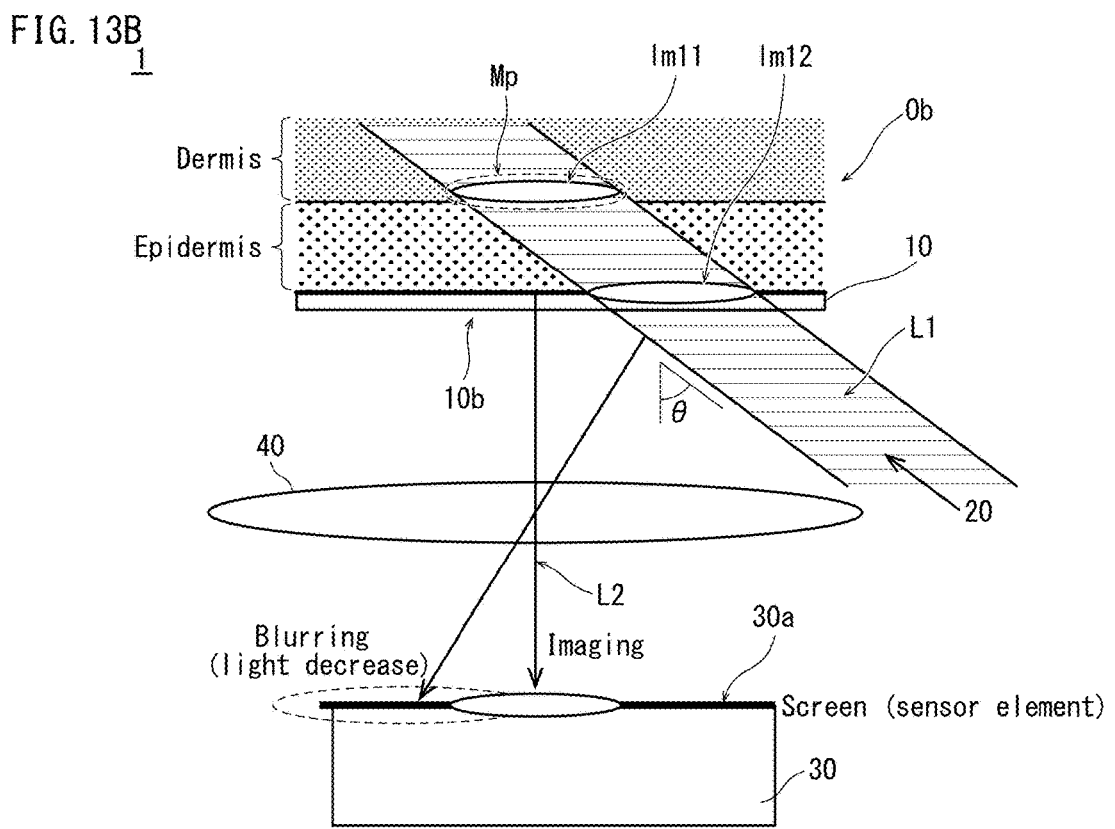
FIG. 13B is a schematic diagram illustrating an optical path from the light emission unit 20 to a photodetector 30 in the substance-in-blood concentration measurement device 1.

In contrast, FIG. 13B is a schematic diagram illustrating an optical path from the light emission unit 20 to the photodetector 30 in the substance-in-blood concentration measurement device 1. As illustrated in FIG. 13B, the substance-in-blood concentration measurement device 1 is similar in that the laser beam L1 emitted from the light emission unit 20 is incident on the living body Ob at the incident angle θ along an optical path towards the measurement target portion Mp of the living body Ob, and a reflected light component Im12 from the skin surface is generated in addition to a reflected light component Im11 from a portion of the living body to be measured inwards of the skin surface that is the measurement target portion Mp, where absorption by blood sugar may occur.

However, in the substance-in-blood concentration measurement device 1, of these reflected light components Im11, Im12, the imaging lens 40 causes mainly the reflected light component Im11 from the inwards portion of the living body to be imaged on the screen 30a of the photodetector 30. The reflected light component Im12 from the skin surface is incident on the imaging lens 40, but the incident angle on the imaging lens 40 different from that of the reflected light component Im11 from the inwards portion of the living body, and therefore is guided outside the area of the screen 30a of the photodetector 30 or even if guided within the area of the screen 30a of the photodetector 30 is not focused (is diffuse), which results in a decreased amount of light and a decrease in signal strength detected by the photodetector 30. As a result, the influence of the reflected light component Im12 from the skin surface detected as noise has a small effect on optical measurement.

That is, in the substance-in-blood concentration measurement device 1, mainly the reflected light component Im11, which is from the portion of the living body inwards of the skin surface that is the measurement target is imaged on the screen 30a of the photodetector 30 to affect light measurement by the photodetector 30, and therefore, when compared to the reference example, higher correlation with SMBG blood sugar level measurement results and higher reproducibility of measurement results were obtained.

Thus, when compared to the conventional device 1X that uses a waveguide, the substance-in-blood concentration measurement device 1 reduces a false signal (noise) component of reflected light scattered from the skin surface, improving S/N ratio. Further, therefore, highly accurate light measurement is normally possible regardless of skin surface conditions, which vary from subject to subject and measurement to measurement. Further, by adjusting the position of the photodetector, it is possible to change the optical path length L on the light receiving side, making it possible to achieve the effect of being able to handle measurement targets having thick skin.

<Review>

As described above, the substance-in-blood concentration measurement device 1 according to Embodiment 1 is for measuring concentration of a substance in blood of the living body Ob, and includes: the target placement unit 10 on which the living body Ob that includes the measurement target portion Mp is placed; the light emission unit 20 that irradiates the measurement target portion Mp with the laser beam L1 from the rear surface 10d side opposite the body placement surface (front surface 10a) side of the target placement unit 10; the photodetector 30 that receives the reflected light L2 of the laser beam L1 reflected from the measurement target portion Mp and detects intensity of the reflected light L2; and the condenser lens 40 disposed on the optical path Op2 of the reflected light L2 between the measurement target portion Mp and the photodetector 30. On the optical path Op2 from the measurement target portion Mp to the photodetector 30, in a section from the target placement unit 10 to the photodetector 30, the reflected light L2 propagates through space, except where transmitted through the condenser lens 40, and the condenser lens 40 forms an image of the reflected light L2 on the photodetector 30.

According to this structure, high accuracy measurement may be stably performed regardless of changes in state of the measurement target and irradiation conditions of the laser beam. As a result, it is possible to eliminate the work of adjusting the optical system for each living body or each measurement in routine blood sugar level measurement performed by a patient, thereby realizing a noninvasive and simple measurement method.

Embodiment 2

The substance-in-blood concentration measurement device 1 according to Embodiment 1 includes the target placement unit 10, the light emission unit 20, the photodetector 30, and the imaging lens 40, where the imaging lens 40 forms an image on the photodetector 30 of the reflected light L2 reflected from the measurement target portion Mp.

However, the specific structure for the imaging lens 40 to form an image on the photodetector 30 of the reflected light L2 reflected from the measurement target portion Mp is not limited to this example, and may be embodied differently.

Figure 14:
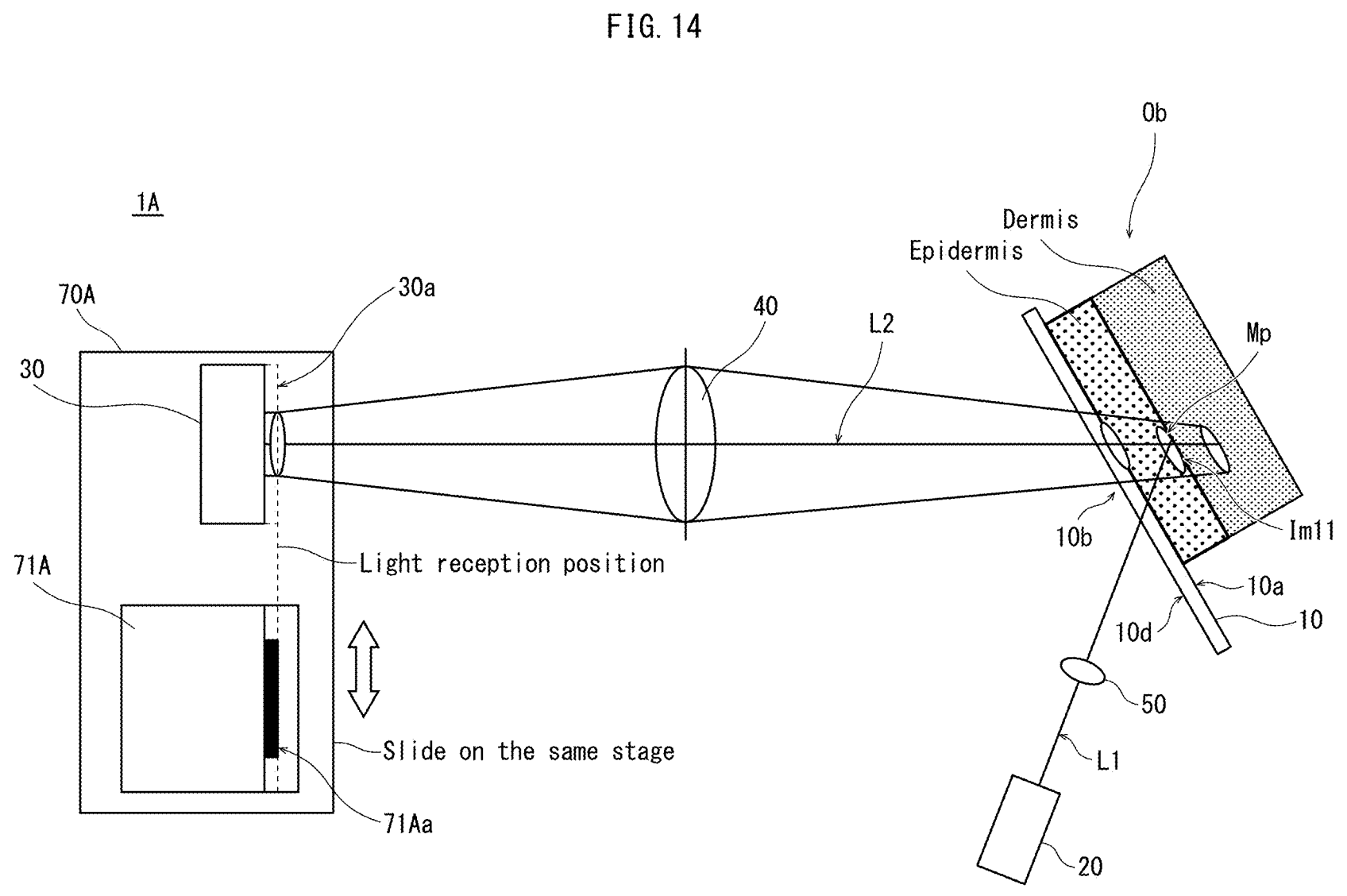

The following describes a substance-in-blood concentration measurement device 1A according to Embodiment 2, with reference to the drawings. FIG. 14 is a schematic diagram illustrating structure of the substance-in-blood concentration measurement device 1A according to Embodiment 2. In FIG. 14, the same structure as in the substance-in-blood concentration measurement device 1 is indicated by the same reference signs, and description thereof is not repeated here.

In the substance-in-blood concentration measurement device 1A according to Embodiment 2, in addition to the structure of the substance-in-blood concentration measurement device 1, a two-dimensional imaging means 71A is added that can be arranged so that position relative to the measurement target portion Mp is equivalent to that of the photodetector 30, the two-dimensional imaging means 71A receiving the reflected light Im11 reflected from the measurement target portion Mp and detecting whether or not an image based on the reflected light Im11 is formed.

The two-dimensional imaging means 71A is a two-dimensional infrared imaging element array in which light receiving elements capable of detecting mid-infrared light are arranged in a matrix on a light receiving surface 71Aa. As illustrated in FIG. 14, the two-dimensional imaging means 71A is integrated with the photodetector 30 to form a light detection unit 70A, and the light detection unit 70A has a structure that allows sliding in a direction perpendicular to the optical path L2 from the measurement target portion Mp to the imaging lens 40. When the two-dimensional imaging means 71A is positioned on the optical path L2, the position of the light receiving surface 71Aa of the two-dimensional imaging means 71A relative to the measurement target portion Mp is equivalent to the position of the screen 30a of the photodetector 30 relative to the measurement target portion Mp when the photodetector 30 is positioned on the optical path L2.

According to this structure, a process of adjusting optical path length from the measurement target portion Mp to the photodetector 30 for the purpose of imaging the reflected light Im11 from the measurement target portion Mp on the photodetector 30 may be performed by replacing the photodetector 30 with the two-dimensional imaging means 71A.

Figure 15:
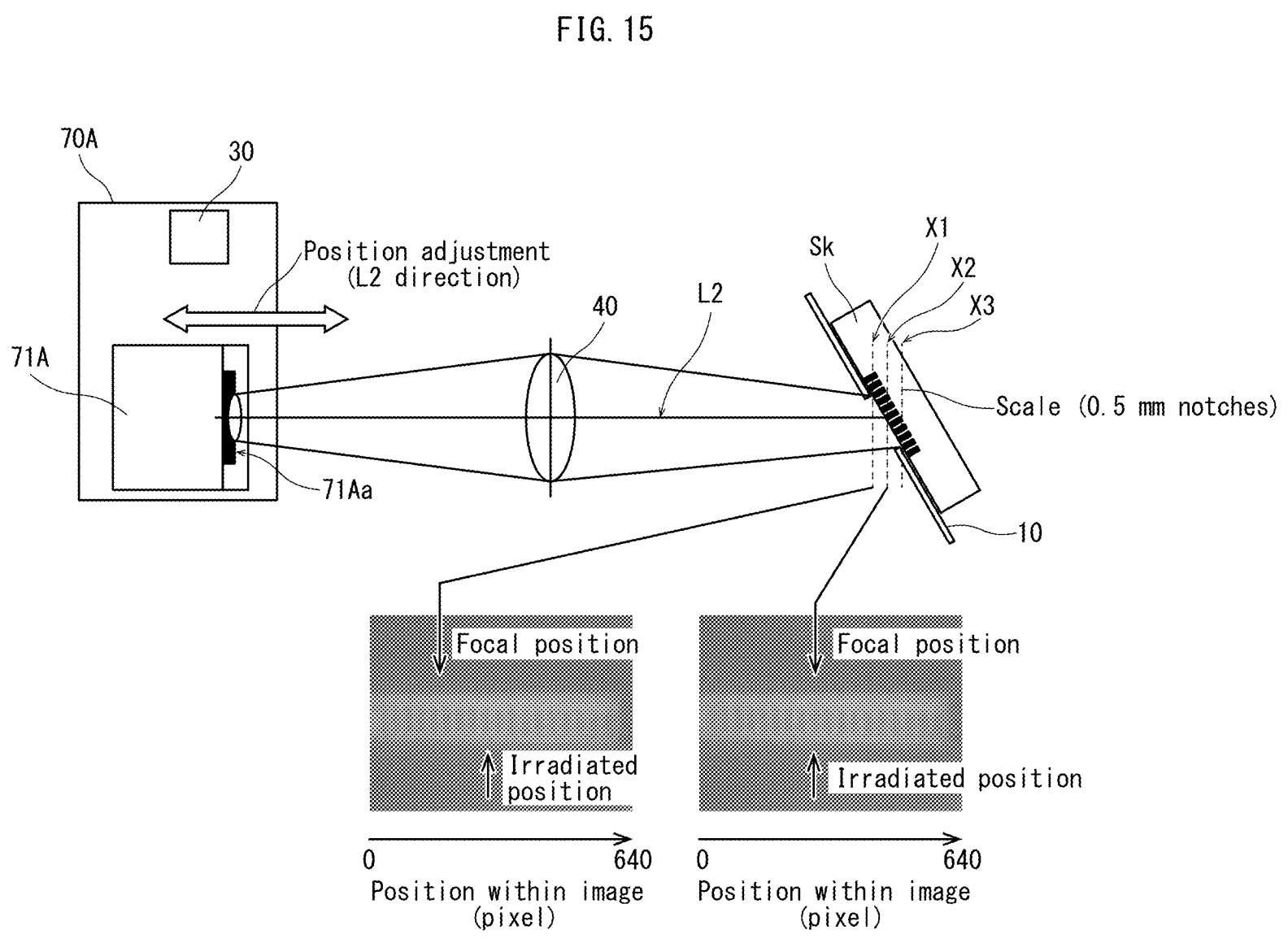

FIG. 15 is a schematic diagram illustrating an operation adjusting optical path length from the measurement target portion Mp to the photodetector 30, according to the substance-in-blood concentration measurement device 1A.

In the optical path length adjustment process, as illustrated in FIG. 15, first, the light receiving surface 71Aa of the two-dimensional imaging means 71A is arranged on the optical path L2 in a position relative to the measurement target portion Mp, the position being equivalent to the position of the screen 30a of the photodetector 30 relative to the measurement target portion Mp on the optical path L2.

Next, in this state, the two-dimensional imaging means 71A is caused to receive light reflected from the measurement target portion Mp and detects whether or not an image based on the reflected light is formed. When not formed, position of the two-dimensional imaging means 71A is gradually moved on the optical path L2 while repeating detection of whether or not the imaging occurs.

Specifically, focal position of a memory image is changed by scanning the two-dimensional imaging means 71A along the optical path L2. This is determined by image analysis, and the position of the two-dimensional imaging means 71A when the irradiation position and focal position that are tested in advance match is determined as the imaging position. As illustrated in FIG. 15, whether or not an image is formed is determined by placing a scale marked with increments of 0.5 mm on the target placement unit 10, acquiring an image by the two-dimensional imaging means 71A, and detecting a focal position in the image. At such time, for example, the focal position may be a maximum point of luminance distribution in the image.

In the example illustrated in FIG. 15, at a position X1 on the scale, the focal position in the acquired image and the irradiation position of the laser beam L1 are off-center, and it is determined that a focused image is not formed. At a position X2 on the scale, the focal position in the acquired image and the irradiation position of the laser beam L1 match, and it is determined that a focused image is formed. So the light detection unit 70A is gradually moved in parallel with the optical path L2 until the focal position of the obtained image and the irradiation position of the laser beam L1 match on the optical path L2, and the presence or absence of focused image formation is determined.

After confirming that a focused image is formed, the two-dimensional imaging means 71A is replaced by the photodetector 30, and the optical path length from the measurement target portion Mp to the photodetector 30 is determined.

As described above, the substance-in-blood concentration measurement device IA according to Embodiment 2 includes the two-dimensional imaging means 71A that may be positioned relative to the measurement target portion Mp at a position equivalent to that of the photodetector 30, that receives the reflected light Im11 reflected from the measurement target portion Mp, and that detects whether or not a focused image is formed based on the reflected light Im11.

According to this structure, a process of adjusting optical path length from the measurement target portion Mp to the photodetector 30 for the purpose of imaging the reflected light Im11 from the measurement target portion Mp on the photodetector 30 may be performed by replacing the photodetector 30 with the two-dimensional imaging means 71A. As a result, it is possible to easily configure the substance-in-blood concentration measurement device 1A capable of stably performing highly accurate measurement regardless of change in state of the measurement target and laser beam irradiation conditions.

Embodiment 3

The substance-in-blood concentration measurement device 1, 1A according to Embodiment 1 is configured such that the wavelength of the laser beam L1 emitted from the light emission unit 20 is 9.26 μm, and the blood component to be detected is glucose.

However, wavelength of the laser beam L1 emitted by the light emission unit 20 may be different, depending on the type of blood component to be detected.

The following describes a substance-in-blood concentration measurement device according to Embodiment 3, with reference to the drawings. In the substance-in-blood concentration measurement device according to Embodiment 3, wavelength of the laser beam L1 emitted by the light emission unit 20 may be 8.23±0.05 μm (from 8.18 μm to 8.28 μm), and the blood component is lactic acid. Alternatively, the wavelength may be in a range from −0.05 μm to +0.05 μm from 5.77 μm, 6.87 μm, 7.27 μm, 8.87 μm, or 9.55 μm.

Figure 16:
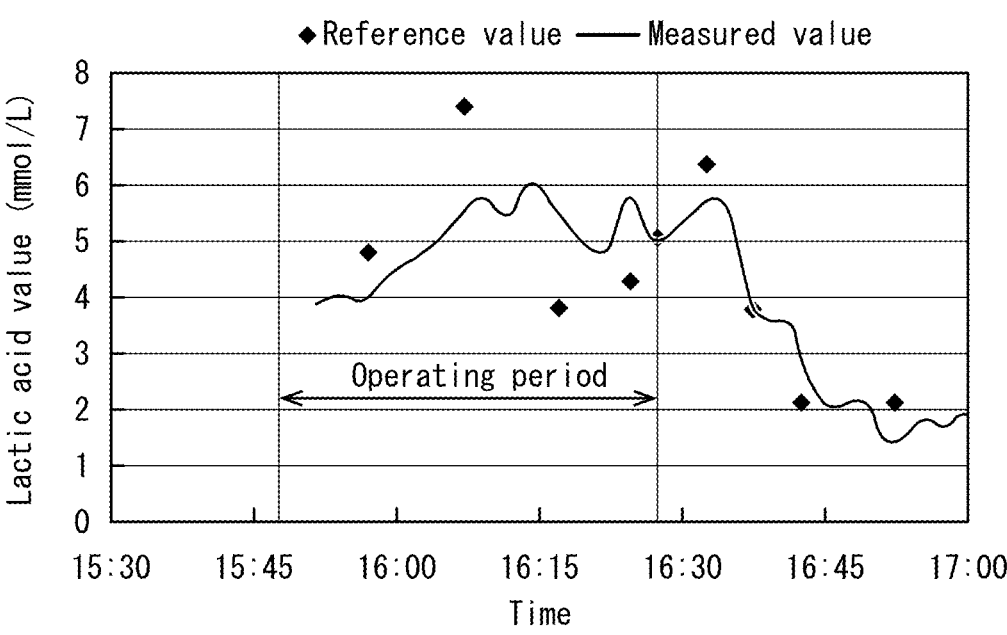
FIG. 16 is a diagram illustrating changes in lactic acid concentration measured by a photodetector when wavelength of light emitted from a light emission unit is changed in a substance-in-blood concentration measurement device according to Embodiment 3.

FIG. 16 is a diagram illustrating changes in lactic acid concentration measured by a photodetector when the wavelength of light emitted from the light emission unit 20 is 8.23 μm in the substance-in-blood concentration measurement device according to Embodiment 3. As illustrated in FIG. 16, it was confirmed that the values measured by optical measurement generally correlated with measurement results of lactic acid levels by blood sampling (reference values).

In order to change the wavelength of light emitted by the light emission unit 20, it is necessary to change the oscillation wavelength of the OPO 22 of the light emission unit 2, which can be realized by changing a phase matching condition of the nonlinear crystal 223 in the OPO 22, or by changing the OPO 22 to one that has a different phase matching condition of the nonlinear crystal 223.

Further, in the light emission unit 20, a plurality of variants of the OPO 22 may be selectively used to selectively emit wavelengths of the laser beam L1 to measure a plurality of types of blood component.

The substance-in-blood concentration measurement device according to Embodiment 3 is different from a structure that adopts an optical system using waveguides in which width, thickness, etc., of an optical path depends on the wavelength of light to be guided in that, for example, the optical system consisting of the condenser lens 50, the target placement unit 10, the imaging lens 40, and the photodetector 30 capable of detecting mid-infrared light is shared with a measurement device for blood components other than glucose.

As described above, according to the substance-in-blood concentration measurement device according to Embodiment 3, different types of blood component may be detected by changing the wavelength of the laser beam L1 emitted by the light emission unit 20. Alternatively, a plurality of different blood components may be detected by selectively emitting the laser beam L1 at different wavelengths with the same measurement device. As a result, a much simpler measurement device may be realized for routine blood sugar level measurement performed by the patient.

<<Modifications>>

As above, specific structures of the present disclosure are described as example embodiments, but the present disclosure is not limited to the above embodiments except for essential characterizing features. For example, an embodiment realized by applying various modifications that a person skilled in the art could conceive of to an embodiment described above, and an embodiment realized by any combination of constituent elements or functions of embodiments described above are also included in this disclosure, as long as they do not depart from the scope of the present invention.

(1) In an embodiment described above, the substance-in-blood concentration measurement device is described in which an example optical system includes the imaging lens 40 between the measurement target portion Mp and the photodetector 30. However, the substance-in-blood concentration measurement device according to the present disclosure may be configured with a different light-receiving optical system, as long as the reflected light L2 reflected from the measurement target portion Mp of the living body Ob is imaged on the photodetector 30. For example, a structure using a plurality of lenses or a structure in which a mirror is arranged on the optical path may be used.

(2) According to an embodiment described above, the blood component to be detected by the substance-in-blood concentration measurement device is glucose or lactic acid, for example. However, the blood component detectable by the substance-in-blood concentration measurement device according to the present disclosure is not limited to the above examples, and the device can be widely used for other detection targets, by changing the wavelength of the laser beam L1 emitted by the light emission unit 20 according to the type of blood component.

(3) According to an embodiment described above, the photodetector 30 is an infrared sensor comprising a single light receiving element able to detect mid-infrared light However, the photodetector 30 may be a two-dimensional infrared imaging element array in which a plurality of light receiving elements able to detect mid-infrared light are arranged in a matrix on a light receiving surface. As a result, the process of adjusting the optical path length from the measurement target portion Mp to the photodetector 30 for imaging light reflected from the measurement target portion Mp on the photodetector 30 may be performed using the photodetector 30 itself. Specifically, in the optical path length adjustment process, the photodetector 30 is made to receive light reflected from the measurement target portion Mp, detect whether or not a focused image is formed based on the reflected light, and if not, position of the photodetector 30 on the optical path L2 is gradually changed while repeatedly detecting whether or not a focused image is formed. As a result, the process of adjusting the optical path length from the measurement target portion Mp to the photodetector 30 may be performed by the photodetector 30 itself, simplifying the device when compared to Embodiment 2.

(4) According to an embodiment described above, in the substance-in-blood concentration measurement device 1, the light emission unit 20 emits the laser beam L1 towards the measurement target portion Mp from the rear surface 10*d* side opposite the body placement surface (front surface 10*a*) side of the target placement unit 10, and the photodetector 30 receives the reflected light L2 from the measurement target portion Mp irradiated by the laser beam L1 emitted from the rear surface 10*d* side of the target placement unit 10.

However, the light emission unit 20 may be configured to irradiate the measurement target portion Mp with the laser beam L1 from the front surface 10*a* side of the target placement unit 10. Further, the photodetector 30 may be configured to receive the reflected light L2 from the measurement target portion of the laser beam L1 emitted from the front surface 10*a* side of the target placement unit 10.

In such a case, for example, a structure may be used in which the measurement target portion Mp of the living body Ob is placed facing upwards on the target placement unit 10, and a plate that transmits the laser beam L1 slightly compresses the living body Ob from above, thereby defining the height of the measurement target portion Mp relative to the target placement unit 10 (and the light emission unit 20).

Alternatively, a structure may be used in which an optical means or the like is provided to detect position of the measurement target portion Mp by measuring time from emission of the laser beam to reception of light reflected from the measurement target portion Mp of the living body Ob, and feedback is applied such as changing emission direction of the laser beam L1 or condenser distance in substance-in-blood concentration measurement, based on position information of the detected measurement target portion Mp.

According to such a structure, substance-in-blood concentration measurement is made possible by the light emission unit 20 irradiating the measurement target portion Mp with the laser beam L1 from the front surface 10*a* side of the target placement unit 10 without passing through the target placement unit 10.

<<Supplement>>

The embodiments described above are preferred specific examples of the present invention. Numerical values, shapes, materials, constituent elements, arrangements, positions, and connections of constituent elements, processes, order of processes, and the like described above are illustrative examples of embodiments, and are not intended to limit the present invention. Further, among constituent elements of embodiments, those that are not described in independent claims, which represent the highest-level concepts of the present invention, are described as constituent elements constituting preferred embodiments.

Further, the order of processing described above is for illustrative purposes in description of specific embodiments of the present invention, and alternative orders may be used. Further, some processes may be performed concurrently (in parallel) with others.

In order to facilitate understanding of the invention, constituent elements in the drawings used in description of the embodiments are not necessarily drawn to scale. Further, the present invention is not limited to the description of the above embodiments, and may be modified as appropriate without departing from the scope of the present invention. Further, at least a portion of the functions of each embodiment and modification thereof may be combined.

INDUSTRIAL APPLICABILITY

The substance-in-blood concentration measurement device and the substance-in-blood concentration measurement method according to an aspect of the present disclosure may be widely used in medical devices for routine measurement of substance-in-blood states such as blood sugar levels and blood lipid levels in prevention and treatment of lifestyle-related diseases.

REFERENCE SIGNS LIST

1. Substance-in-blood concentration measurement device
10, 10X Target placement unit
20, 20X Light emission unit
21 Light source 22 Optical parametric oscillator
221 Incident-side semi-transmissive mirror
222 Output-side semi-transmissive mirror
223 Nonlinear optical crystal
30 Photodetector
40 Imaging lens (first lens)
50 Condenser lens (second lens)
70A Light detection unit
71A Two-dimensional imaging means
90X Light guide unit
91X Incident-side waveguide
92X Output-side waveguide

The invention claimed is:

1. A substance-in-blood concentration measurement device for measuring concentration of a substance in blood of a living body, comprising:

a target placement surface on which the living body that includes a measurement target portion is placed;

a laser configured to irradiate the measurement target portion with a laser beam, wherein the measurement target portion is a portion of the living body inwards of an epidermis;

a photodetector configured to receive a reflected light component of the laser beam reflected from the measurement target portion and detect intensity of the reflected light; and a first lens disposed on an optical path of the reflected light between the measurement target portion and the photodetector, wherein on the optical path from the measurement target portion to the photodetector, in a section from the target placement surface to the photodetector, the reflected light propagates through space, except where transmitted through the first lens, and the first lens is optically conjugated to focus the reflected light from the measurement target portion onto a light receiving surface of the photodetector such that reflected light from a skin surface of the living body is defocused at the light receiving surface or guided outside an area of the light receiving surface on the photodetector.

2. The substance-in-blood concentration measurement device of claim 1, wherein the laser is configured to irradiate the measurement target portion with the laser beam from a back surface side opposite a body placement side of the target placement surface, and the photodetector is configured to receive the reflected light component of the laser beam reflected from the measurement target portion from the back surface side of the target placement surface.

3. The substance-in-blood concentration measurement device of claim 1, further comprising a second lens disposed on the optical path of the laser beam between the laser and the measurement target portion, the second lens condensing the laser beam on the measurement target portion, wherein on the optical path from laser to the measurement target portion, in a section from the laser to the target placement surface, the laser beam propagates through space, except where transmitted through the second lens.

4. The substance-in-blood concentration measurement device of claim 1, wherein the light receiving surface of the photodetector is separated from the first lens by a defined distance more than a distance from the first lens to a position to which an image of light reflected from a skin surface of the living body is transferred.

5. The substance-in-blood concentration measurement device of claim 1, wherein depth from a skin surface of the living body to the measurement target portion is changed by changing a position of the photodetector.

6. The substance-in-blood concentration measurement device of claim 1, wherein an incident angle of the laser beam to the measurement target portion is different from an emission angle of the optical path from the measurement target portion to the photodetector.

7. The substance-in-blood concentration measurement device of claim 6, wherein the emission angle of the optical path from the measurement target portion to the photodetector is from 0 degrees to 90 degrees from the normal to a surface of the target placement surface on which the living body is placed, and is different from the incident angle of the laser beam to the measurement target portion.

8. The substance-in-blood concentration measurement device of claim 6, wherein the incident angle of the laser beam to the measurement target portion is 45 degrees or more from the normal to a surface of the target placement surface on which the living body is placed, and the emission angle of the optical path from the measurement target portion to the photodetector is from 0 degrees to 40 degrees from the normal to the surface.

9. The substance-in-blood concentration measurement device of claim 1, wherein wavelength of the laser beam is a defined wavelength selected from a range from 2.5 m to 12 m.

10. The substance-in-blood concentration measurement device of claim 9, wherein modulating the wavelength of the laser beam allows for detection of different types of blood component.

11. The substance-in-blood concentration measurement device of claim 9, wherein the wavelength of the laser beam is a defined wavelength selected from a range from 6.0 m to 12 m, and a blood component to be detected is glucose.

12. The substance-in-blood concentration measurement device of claim 9, wherein the wavelength of the laser beam is a defined wavelength selected from a range from 5.0 m to 12 m, and a blood component to be detected is lactic acid.

13. The substance-in-blood concentration measurement device of claim 1, wherein the photodetector comprises an infrared sensor that outputs an intensity of the reflected light as a one-dimensional value, and the substance-in-blood concentration measurement device further comprises a two-dimensional imaging means that may be disposed in a position relative to the measurement target portion that is equivalent to the position relative to the measurement target portion of the photodetector, the two-dimensional imaging means receiving the reflected light reflected from the measurement target portion to detect whether or not a focused image is formed based on the reflected light.

14. The substance-in-blood concentration measurement device of claim 1, wherein the photodetector is a two-dimensional infrared sensor array in which a plurality of light receiving elements capable of detecting mid-infrared light are arranged in a matrix on a light receiving surface.

15. The substance-in-blood concentration measurement device of claim 1, wherein the target placement surface is provided with a through hole in an area where a surface of the living body comes into contact with the target placement surface, the laser beam is configured to irradiate the surface of the living body through the through hole, and the photodetector is configured to receive the reflected light passing through the through hole.

16. The substance-in-blood concentration measurement device of claim 1, wherein the target placement surface is provided with a concave portion in an area where a surface of the living body comes into contact with the target placement surface, the laser is configured to irradiate the surface of the living body by passing through the target placement surface, and the photodetector is configured to receive the reflected light after passing through the target placement surface.

17. The substance-in-blood concentration measurement device of claim 1, wherein signal strength detected by the photodetector from reflected light from a skin surface is lower than that from the reflected light from the measurement target portion inward of the epidermis.

18. A substance-in-blood concentration measurement method for measuring concentration of a substance in blood of a living body, comprising:

placing the living body that includes a measurement target portion;

irradiating the measurement target portion with a laser beam from a laser, wherein the measurement target portion is a portion of the living body inwards of an epidermis;

optically forming an image of light reflected from the measurement target portion onto a photodetector using a first lens disposed between the measurement target portion and the photodetector, the first lens being optically conjugated to focus the reflected light from the measurement target portion onto a light receiving surface of the photodetector such that reflected light from a skin surface of the living body is defocused at the light receiving surface or guided outside an area of the light receiving surface on the photodetector; and receiving the reflected light with the photodetector and detecting intensity of the reflected light.

19. The substance-in-blood concentration measurement method of claim 18, further comprising condensing the laser beam onto the measurement target portion by using a second lens disposed between the laser and the measurement target portion.

20. The substance-in-blood concentration measurement method of claim 19, wherein, on the optical path from the measurement target portion to the photodetector, in a section from a target placement surface to the photodetector, the reflected light propagates through space, except where transmitted through the first lens, and on the optical path from the laser to the measurement target portion, in a section from the laser to the target placement surface, the laser beam propagates through space, except where transmitted through the second lens.

21. The substance-in-blood concentration measurement method of claim 20, wherein irradiating the measurement target portion is from a back surface side opposite a body placement side of the target placement surface, and receives the reflected light component of the laser beam reflected from the measurement target portion from the back surface side of the target placement surface.

22. The substance-in-blood concentration measurement method of claim 18, further comprising, prior to forming the image, adjusting an optical path length from the measurement target portion to the photodetector so that the light reflected from the measurement target portion forms a focused image on the photodetector.

23. The substance-in-blood concentration measurement method of claim 22, wherein adjusting includes causing a two-dimensional imaging means disposed in a position relative to the measurement target portion that is equivalent to the position relative to the measurement target portion of the photodetector to receive the reflected light reflected from the measurement target portion, and detecting whether or not the focused image is formed based on the reflected light.

24. The substance-in-blood concentration measurement method of claim 18, wherein signal strength detected by the photodetector from reflected light from a skin surface is lower than that from the reflected light from the measurement target portion inward of the epidermis.

\*  \*  \*  \*  \*